(12) United States Patent
Yu et al.

(10) Patent No.: US 7,988,983 B2
(45) Date of Patent: Aug. 2, 2011

(54) MICROENCAPSULATION COATING FOR GLOVES

(75) Inventors: E. Anthony Yu, Medina, OH (US); Stanley J. Gromelski, Canton, OH (US); Paul Cacioli, Eltham South (AU); Richard L. Cox, Massillon, OH (US)

(73) Assignee: Ansell Healthcare Products LLC, Red Bank, NJ (US)

( * ) Notice: Subject to any disclaimer, the term of this patent is extended or adjusted under 35 U.S.C. 154(b) by 1385 days.

(21) Appl. No.: 10/489,157

(22) PCT Filed: Sep. 13, 2002

(86) PCT No.: PCT/US02/29250
§ 371 (c)(1),
(2), (4) Date: Oct. 12, 2004

(87) PCT Pub. No.: WO03/022962
PCT Pub. Date: Mar. 20, 2003

(65) Prior Publication Data
US 2005/0066414 A1    Mar. 31, 2005

Related U.S. Application Data

(60) Provisional application No. 60/322,317, filed on Sep. 13, 2001.

(51) Int. Cl.
*A01N 25/34* (2006.01)
(52) U.S. Cl. ............ 424/402; 424/417; 2/167; 2/168; 264/131
(58) Field of Classification Search .................. None
See application file for complete search history.

(56) References Cited

U.S. PATENT DOCUMENTS

| | | | |
|---|---|---|---|
| 3,516,941 A * | 6/1970 | Matson | 264/4.33 |
| 3,896,807 A | 7/1975 | Buchalter | |
| 4,547,429 A * | 10/1985 | Greiner et al. | 428/402.24 |
| 4,567,065 A | 1/1986 | Schneiderman | |
| 4,622,267 A * | 11/1986 | Riecke | 428/402.21 |
| 4,897,268 A | 1/1990 | Tice et al. | |
| 4,917,920 A * | 4/1990 | Ono et al. | 427/389.9 |
| 4,930,522 A | 6/1990 | Busnel et al. | |
| 4,959,220 A * | 9/1990 | Yamamoto et al. | 424/490 |
| 4,985,064 A | 1/1991 | Redlich et al. | |
| 4,996,052 A | 2/1991 | McIntosh | |
| 5,024,852 A | 6/1991 | Busnel et al. | |
| 5,088,125 A | 2/1992 | Ansell et al. | |
| 5,137,646 A * | 8/1992 | Schmidt et al. | 510/515 |
| 5,138,719 A * | 8/1992 | Orlianges et al. | 2/168 |
| 5,433,953 A | 7/1995 | Tsuei et al. | |
| 5,534,350 A | 7/1996 | Liou | |
| 5,549,924 A | 8/1996 | Shlenker et al. | |
| 5,922,336 A | 7/1999 | Tebbe | |
| 6,527,990 B2 | 3/2003 | Yamashita et al. | |
| 6,550,474 B1 * | 4/2003 | Anderson et al. | 128/200.24 |
| 6,958,148 B1 * | 10/2005 | Green et al. | 424/94.5 |
| 2001/0008874 A1* | 7/2001 | Igari et al. | 504/359 |
| 2002/0192248 A1* | 12/2002 | Victor | 424/401 |
| 2005/0002995 A1 | 1/2005 | Schaller | |
| 2007/0104766 A1 | 5/2007 | Wang et al. | |

FOREIGN PATENT DOCUMENTS

| | | |
|---|---|---|
| DE | 20100269 U1 * | 7/2001 |
| DE | 2010026901 | 7/2001 |
| JP | 05-069110 | 9/1993 |
| JP | 10-130920 A | 5/1998 |
| WO | WO-00/65911 | 11/2000 |

OTHER PUBLICATIONS

Translation of DE 20100269.*
Emollients 1999 Report [online], [retrieved on Sep. 12, 2002]. Retrieved from the Internet <URL: http://www.creative-developments.co.uk/papers/Emollients%201999.html>.
Index to Papers and Presentations [online], [retrieved on Sep. 12, 2002]. Retrieved from the Internet <URL: http://www.creative-developments.co.uk/papers.html>.
Emollients/Cosmetic Oils—Lipovol Natural Oils [online], [retrieved on Sep. 13, 2002]. Retrieved from the Internet <URL http://www.lipochemicals.com/doc/i3.htm>.
International Search Report for International Application No. PCT/US02/29250.
"Supplementary European Search Report mailed Jan. 20, 2010", 02773387.2, 3.

* cited by examiner

*Primary Examiner* — Robert A Wax
*Assistant Examiner* — Hasan Ahmed
(74) *Attorney, Agent, or Firm* — Moser Taboada

(57) ABSTRACT

The present invention provides for a coating having microcapsules for use with a glove. The coating improves both wet and dry and donnability of the glove. The coating comprises microcapsules, water and a polyurethane for application to a glove.

13 Claims, 25 Drawing Sheets

MICROENCAPSULATION COATING FOR GLOVES

FIELD OF THE INVENTION

The present invention relates to an easily donnable glove produced using a novel coating formulation that includes a microencapsulated material.

BACKGROUND OF THE INVENTION

Medical, surgical and other gloves, made of a rubber latex, are typically made so that these rubber articles tightly conform to the human hand. Because of this tight fit, such gloves are typically lubricated on the skin-contacting inner surface in order to facilitate donning of the gloves. The standard lubricant utilized for this purpose is dusting powder, e.g., cross-linked corn starch.

Various methods have been proposed to provide slip finishes on rubber articles, thus seeking to avoid the use of powdered internal surface lubricants. For example, the surface of a rubber glove can be halogenated with bromine or chlorine to make it slippery. This treatment, however, has certain disadvantages well-known in the art and typically does not produce a glove that is easier to don than a glove internally coated with dusting powder. One prior art glove provides a slip finish comprising a rubber latex blended with a resin latex. This approach, while lowering the coefficient of friction of the rubber glove, does not significantly improve donnability. Yet another prior art glove is made with granular material deposited on the inner, skin-contacting surface of a single-layer vinyl or silicone glove in order to reduce the frictional contact between the glove layer and the skin of the wearer. Use of this glove, however, results in the granular material being abraded from the inner glove surface thus generating loose particulate matter.

One example of the prior art is a therapeutic glove for dry hands. The glove comprises two layers of mesh or scrim, an upper palm panel or layer and a lower back of the hand or layer. The scrim is heat fused at the borders of all five fingers and the mesh layers have a coating of dried polyvinyl alcohol. As the glove is worn and subsequently moistened, most or all of the polyvinyl alcohol coating dissolves, leaving a mixture of dissolved polyvinyl alcohol and water, held captive in the mesh in a somewhat slurry or slush form. In addition, as the outermost part of the slurry begins to dry by normal evaporation, the inner parts of the slurry disposed between the outer part of the glove and the skin continue to moisturize the skin. One significant disadvantage of this type of prior art is the lack of dexterity in the hands and fingers for use in fine motor function. Another disadvantage is the use of polyvinyl alcohol attached to the interior of the glove. The hand must first be wetted or moistened for the polyvinyl alcohol to dissolve. In addition, the exterior of the glove must be moistened for continued dissolution of the polyvinyl alcohol.

It is therefore desirable to have a glove with moisturizing properties, which is easily donnable on both dry and damp hands, made by a process that does not result in loose particulate matter on the inside of the gloves.

Accordingly, there is a need to have a glove that provides moisturizer to the skin yet provides the user the ability to maintain dexterity in the hands and fingers for fine motor function.

It is also advantageous to have a glove that does not rely on dusting powders and or on an internal surface lubricant for donnability, but instead applies a surface lubricant in a new and improved way.

It is further advantageous to have a glove that does not require moisture or wetting of the hand or interior of the glove prior to donning of the glove.

SUMMARY OF THE INVENTION

In one embodiment, the present invention provides a composition including a mixture of a microcapsule, water, and a polyurethane. The microcapsule includes a low viscosity hydrocarbon, fragrance, vitamins, and a microcapsule coating. The microcapsule coating includes a polyacetal urea.

In another embodiment, the present invention provides a glove coating including a mixture of a microcapsule, water, and a polyurethane. The microcapsule includes a low viscosity hydrocarbon, fragrance, vitamins, and a microcapsule coating. The microcapsule coating includes a polyacetal urea.

In another embodiment, the present invention provides a composition including a mixture of a microcapsule, water, and a polyurethane. The microcapsule includes hydrogenated polyisobutene, vanilla fragrance, Vitamin A Palmitate, Vitamin E Acetate, and a microcapsule coating. The microcapsule coating includes a polyoxymethylene urea.

In another embodiment, the present invention provides a glove coating including a mixture of a microcapsule, water, and a polyurethane. The microcapsule includes hydrogenated polyisobutene, vanilla fragrance, Vitamin A Palmitate, Vitamin E Acetate, and a microcapsule coating. The microcapsule coating includes a polyoxymethylene urea.

In another embodiment the present invention provides a glove including an outside surface and an inside skin contacting surface including microcapsules. The microcapsule includes a low viscosity hydrocarbon, fragrance, vitamins, and a microcapsule coating. The microcapsule coating includes a polyacetal urea.

In another embodiment the present invention provides a glove including an outside surface and an inside skin contacting surface including microcapsules. The microcapsule includes hydrogenated polyisobutene, vanilla fragrance, Vitamin A Palmitate, Vitamin E Acetate, and a microcapsule coating. The microcapsule coating includes a polyoxymethylene urea.

In another embodiment the present invention utilizes a microcapsule including a low viscosity hydrocarbon, fragrance, moisturizers, dyes and vitamins to improve the donnability of rubber gloves. The microcapsules may be applied to the glove in various ways to achieve a layer on the hand-contacting surface that will improve the donnability, odor and moisturizing properties of the glove. As the gloves are donned on the hand, the microcapsules rupture to provide moisturizers and vitamins to the hand. The present invention further provides for a process for manufacturing a glove with increased donning capabilities that includes the use of microcapsules in a dip coating over the rubber latex glove layer.

In another embodiment the present invention utilizes a microcapsule including hydrogenated polyisobutene, fragrance, moisturizers, dyes and vitamins to improve the donnability of rubber gloves. The microcapsules may be applied to the glove in various ways to achieve a layer on the hand-contacting surface that will improve the donnability, odor and moisturizing properties of the glove. As the gloves are donned on the hand, the microcapsules rupture to provide moisturizers and vitamins to the hand. The present invention further provides for a process for manufacturing a glove with increased donning capabilities that includes the use of microcapsules in a dip coating over the rubber latex glove layer.

There is provided, in accordance with the principles of the present invention, a glove having moisturizing properties that is easily donnnable on both wet and dry hands that does not result in loose particulate matter.

There is further provided, according to the principles of the present invention, a glove that provides moisturizer to the skin while enabling the user to maintain fine motor function in both the hands and fingers.

DETAILED DESCRIPTION OF THE INVENTION

Figure 1:
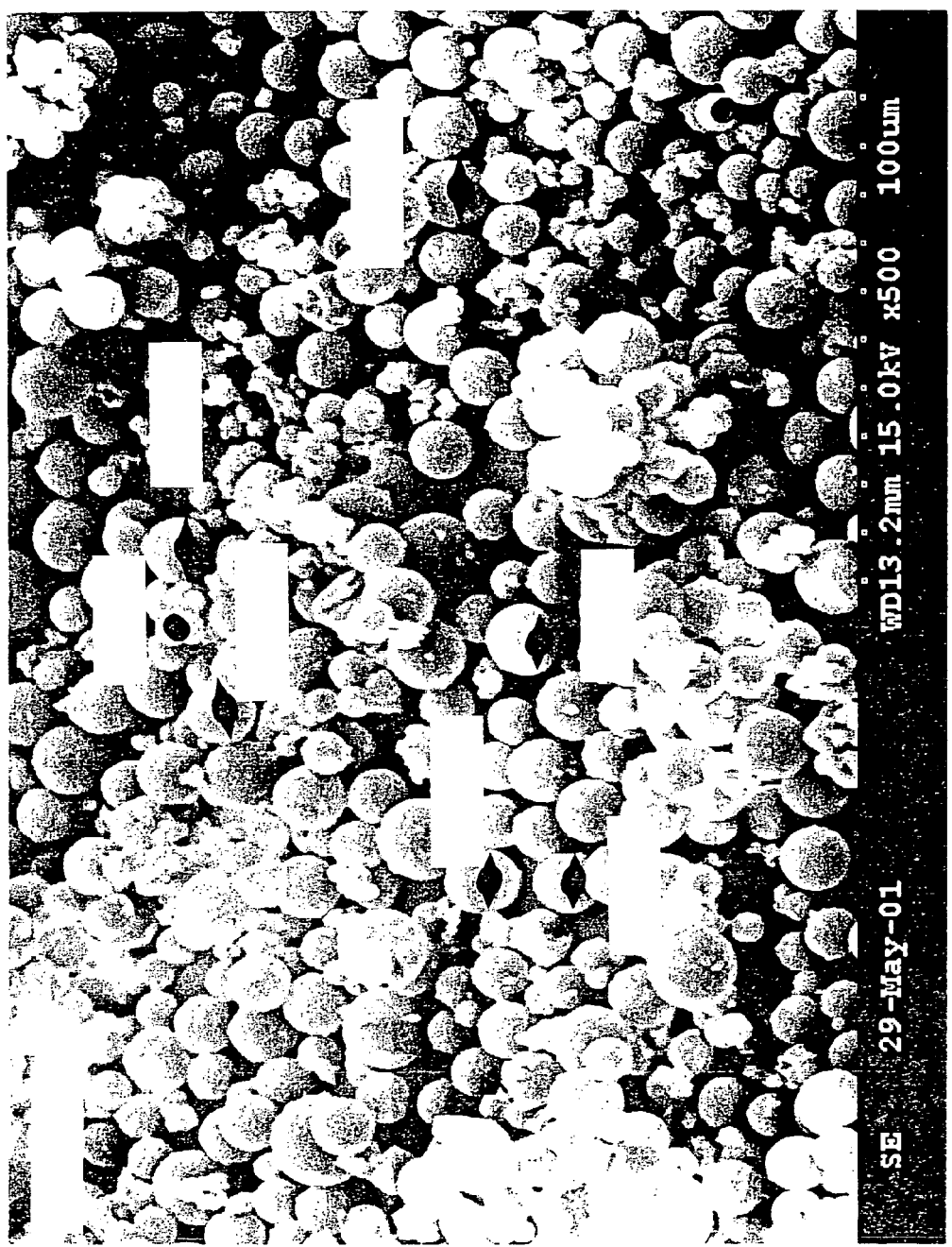
FIG. 1 is a scanning electron photomicrograph of the microcapsules according to the present invention.
Figure 2:
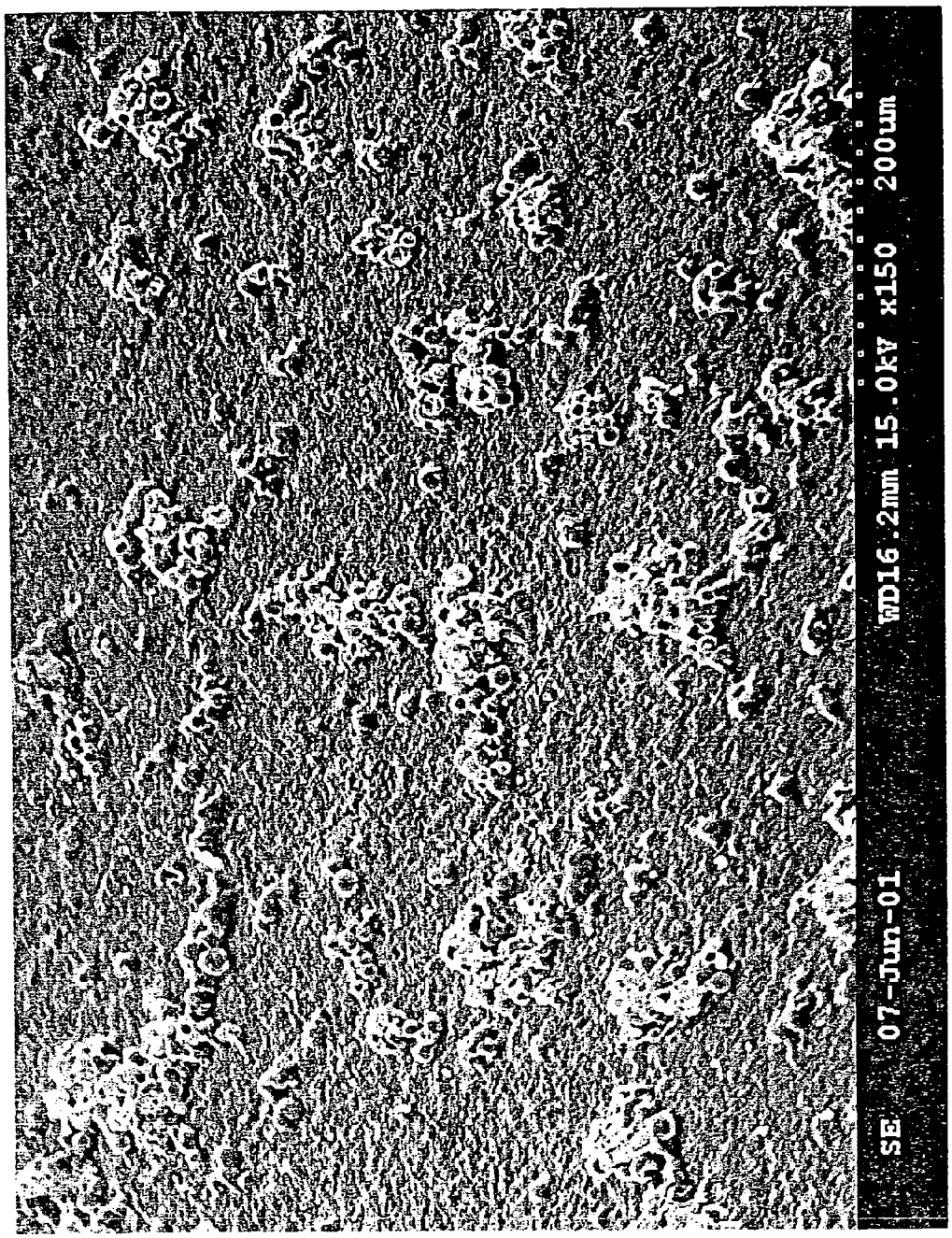
FIG. 2 is a scanning electron photomicrograph of a tube sample with a 1 weight % microcapsule overdip at a 0% stretch according to the present invention.
Figure 3:
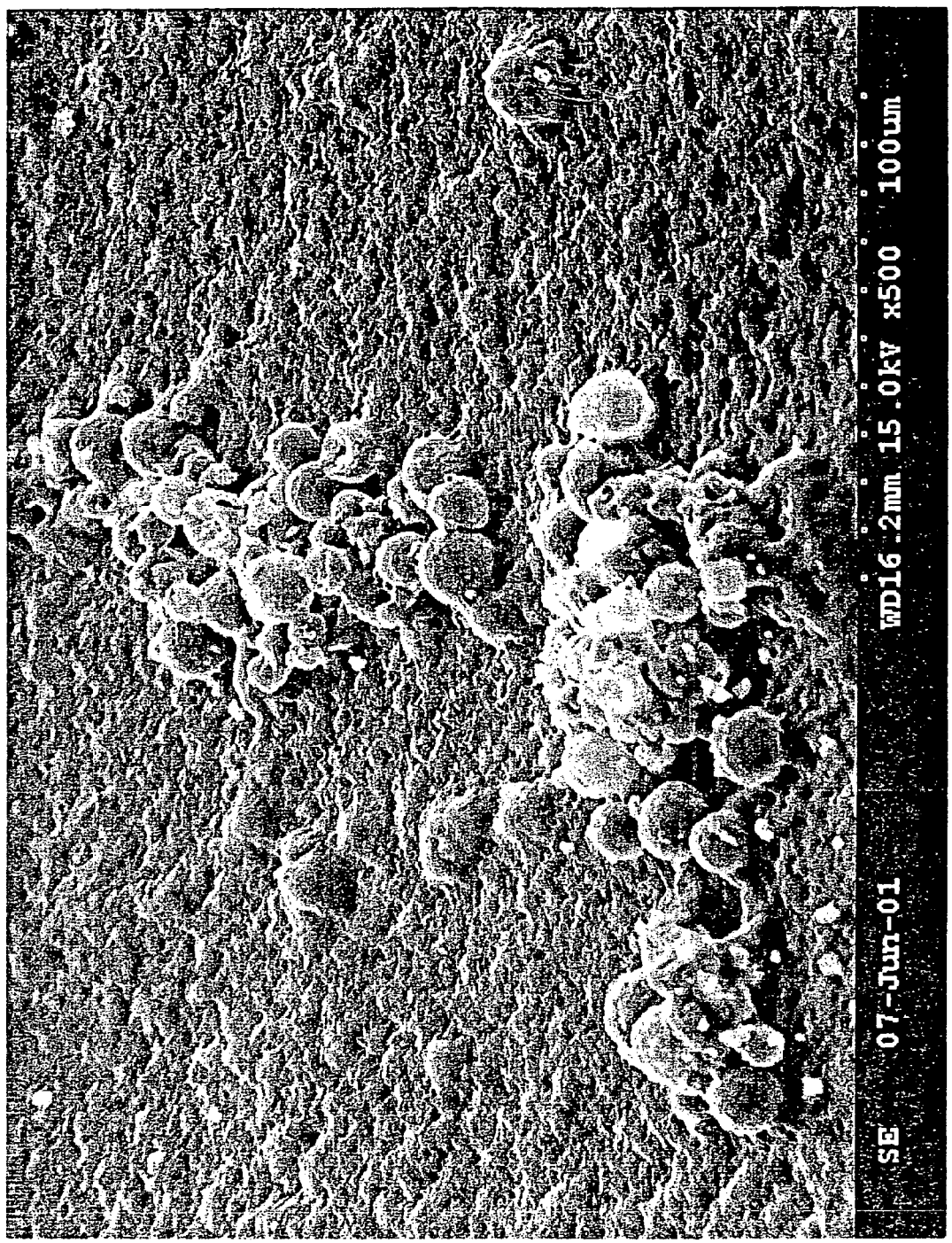
FIG. 3 is a scanning electron photomicrograph of a tube sample with a 1 weight % microcapsule overdip at a 0% stretch according to the present invention.
Figure 4:
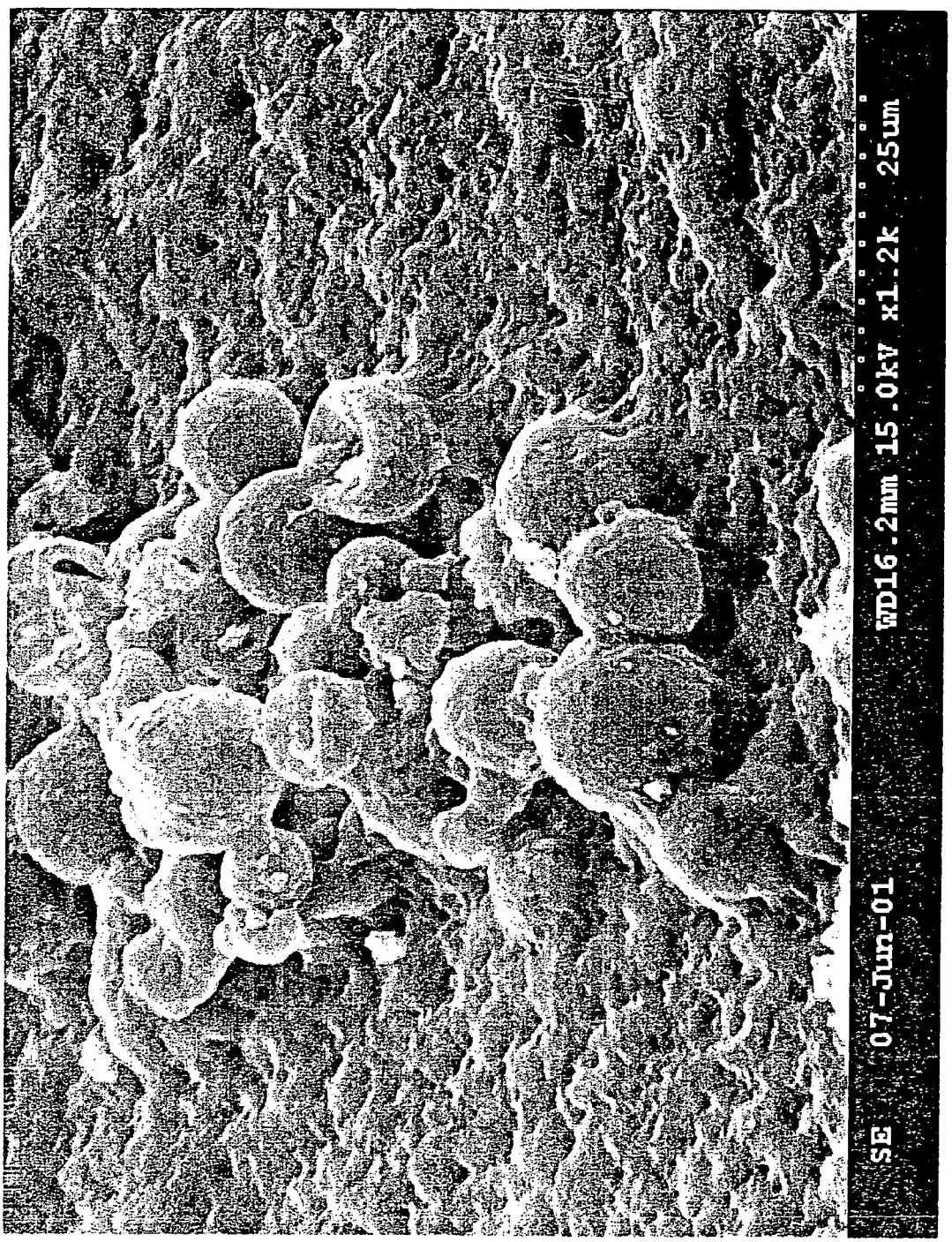
FIG. 4 is a scanning electron photomicrograph of a tube sample with a 1 weight % microcapsule overdip at a 0% stretch according to the present invention.
Figure 5:
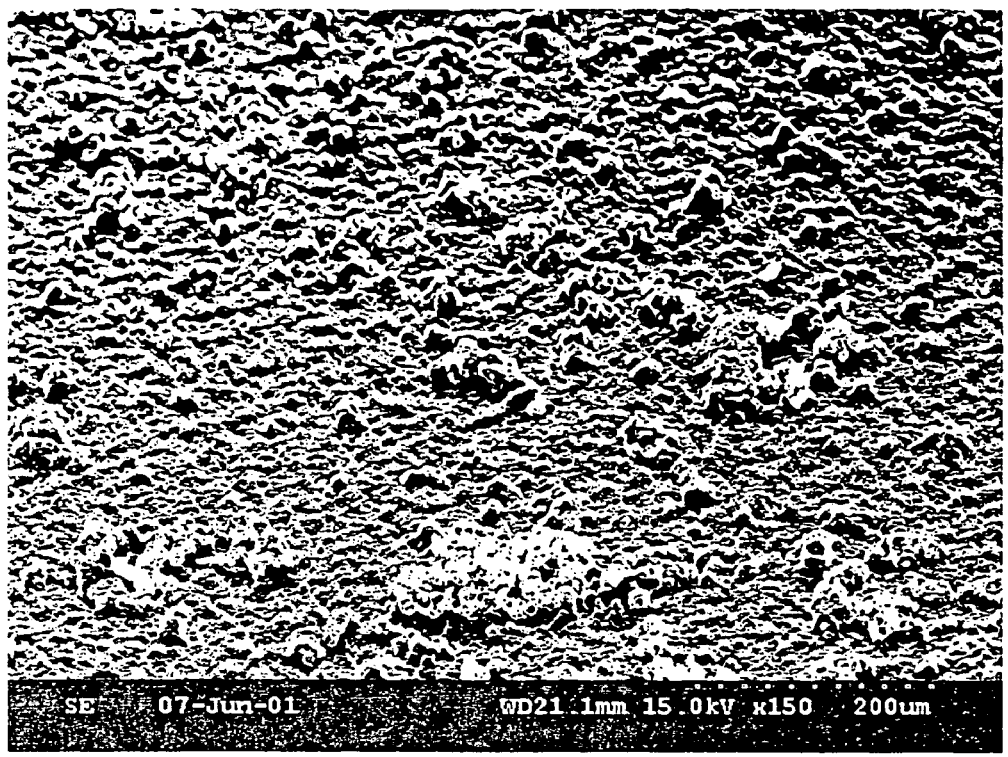
FIG. 5 is a scanning electron photomicrograph of a tube sample with a 1 weight % microcapsule overdip at a 500% stretch according to the present invention.
Figure 6:
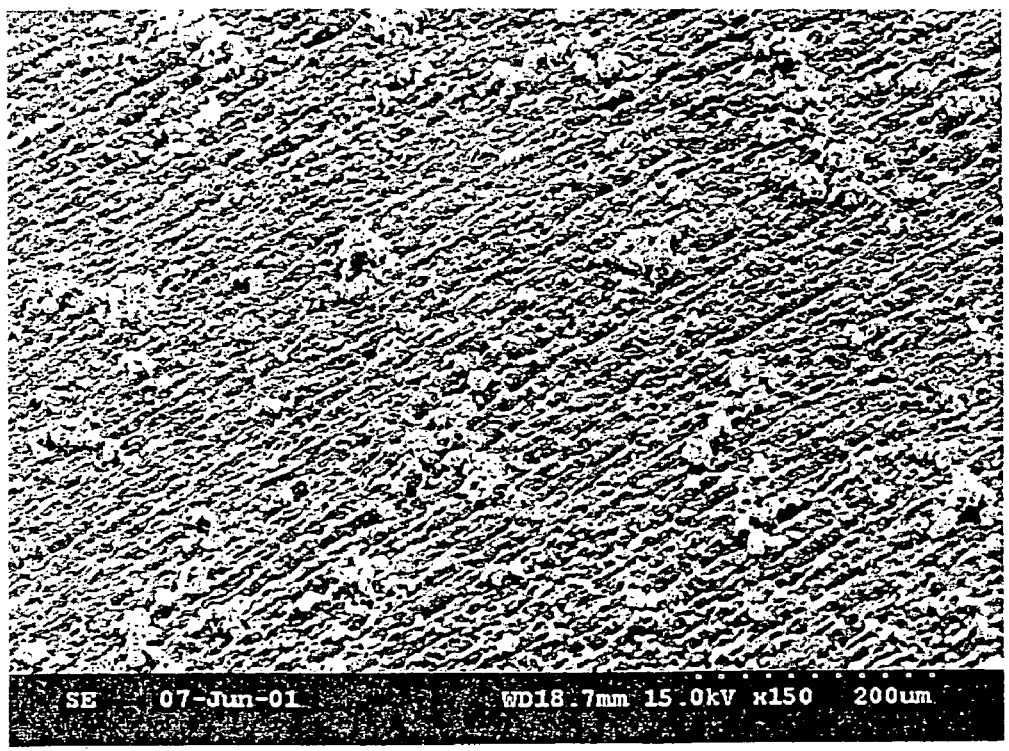
FIG. 6 is a scanning electron photomicrograph of a tube sample with a 1 weight % microcapsule overdip at a 5×700% stretch according to the present invention.
Figure 7:
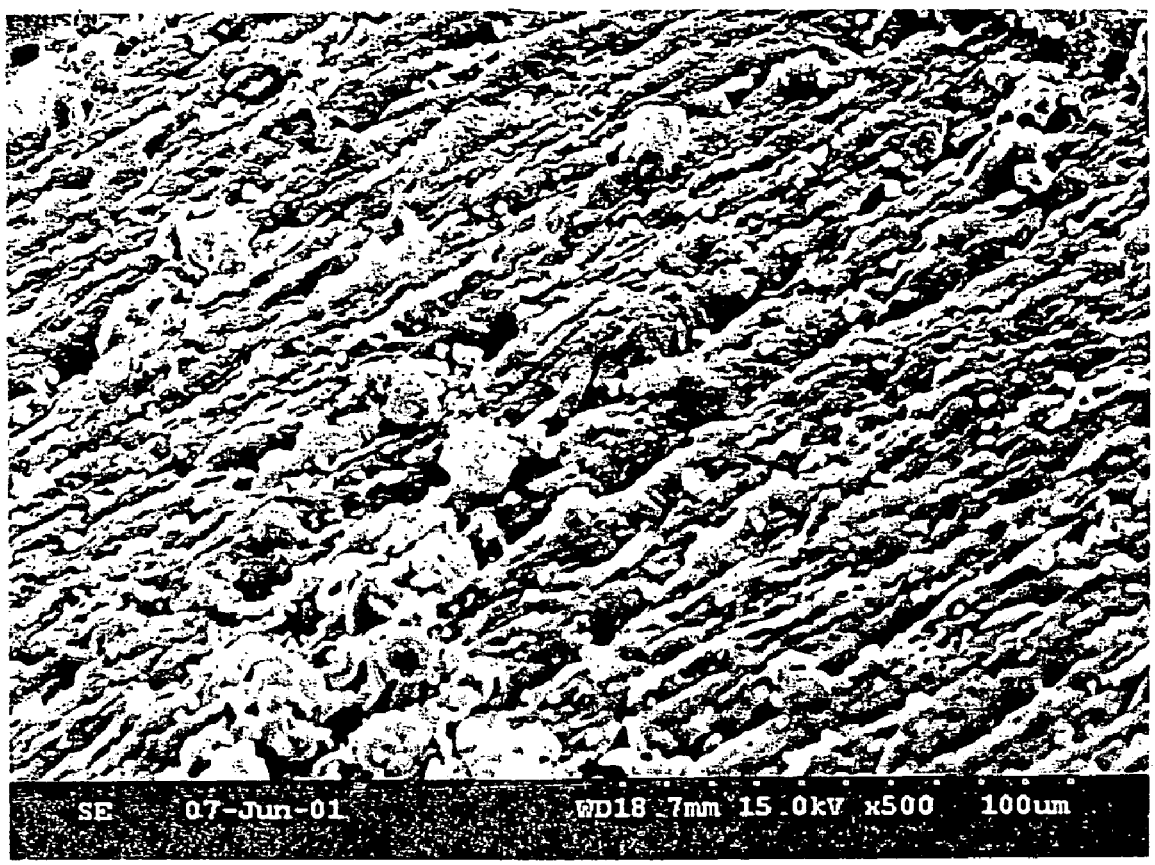
FIG. 7 is a scanning electron photomicrograph of a tube sample with a 1 weight % microcapsule overdip at a 5×700% stretch according to the present invention.
Figure 8:
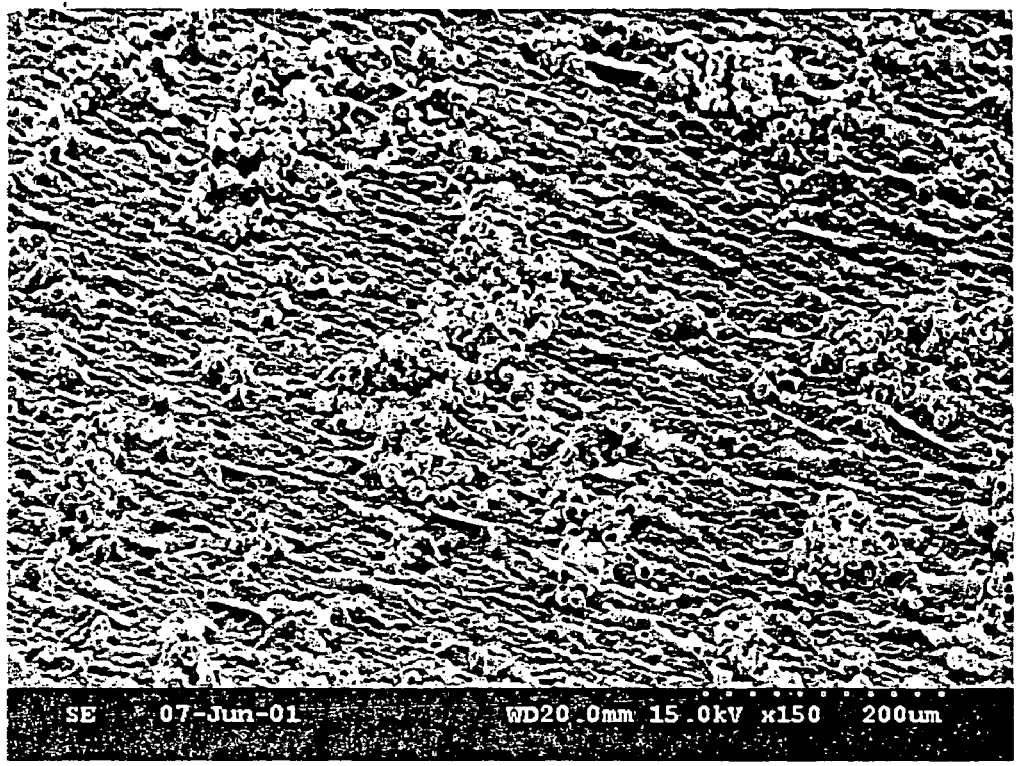
FIG. 8 is a scanning electron photomicrograph of a tube sample with a 1 weight % microcapsule overdip after a break according to the present invention.
Figure 9:
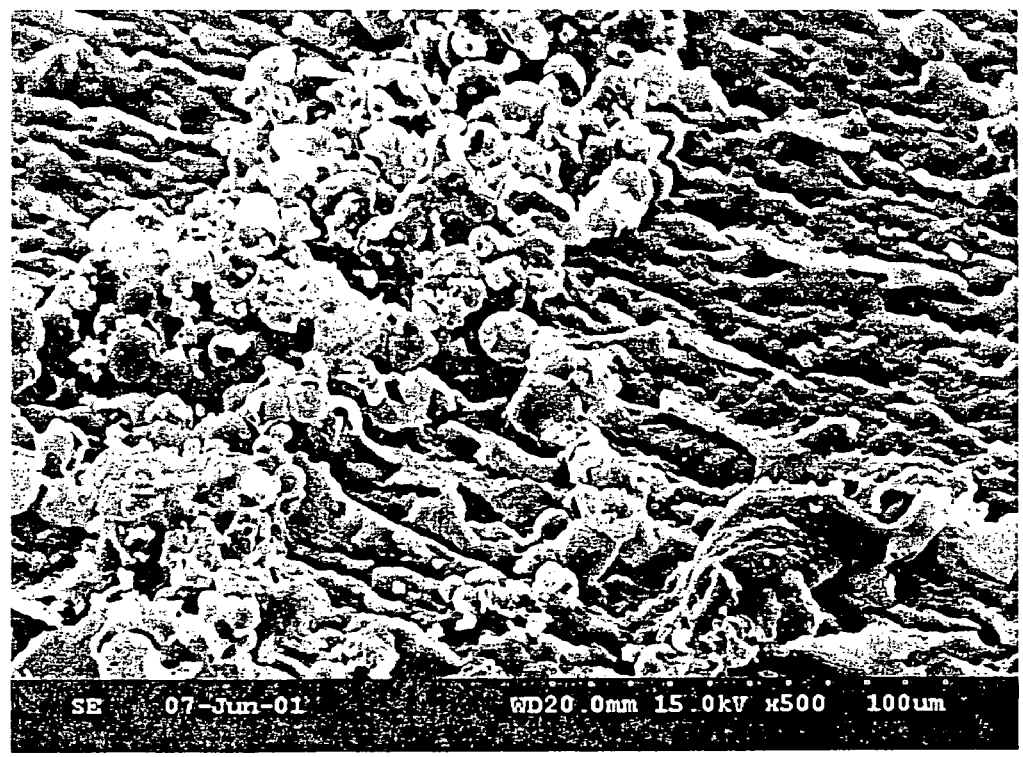
FIG. 9 is a scanning electron photomicrograph of a tube sample with a 1 weight % microcapsule overdip after a break according to the present invention.

There is provided according to the principles of the present invention, a glove coating including microcapsules having materials contained within the microcapsules used to enhance donning, increase moisturizing properties and impart a pleasant odor. The microcapsules may be applied to the glove in the donning coating overdip, as a direct application to the wet latex film, in a compound within the latex, or in a slurry as a final dip.

The embodiments set forth in Tables 1-6 below use the microcapsules in the donning coating overdip. Generally, microcapsules of the present invention include a low viscosity hydrocarbon, fragrance, vitamins, moisturizers, dyes and a microcapsule coating having a polyacetal urea. Alternatively, the microcapsule coating may include polyamides and/or gelatin. Examples of low viscosity hydrocarbons include hydrogenated polyisobutene, hydrogenated polybutene, hydrogenated polydecene, and the like. The embodiments listed below are but one way in which the microcapsules may be used and represent concentrations of the microcapsule in an overdip solution. An overdip solution is one example in which an embodiment of the present invention may be applied to the glove and involves dipping the formed rubber glove into a solution containing the microcapsules. The microcapsules are deposited in a layer which becomes a part of the inside donning surface of the glove. The embodiments set forth below include microcapsules containing moisturizing and fragrance materials, the microcapsules in a range from about 1 weight % to about 5 weight % of the overdip solution containing water and polyurethane. The microcapsules are attached to the inside donning surface of the glove such that, as the glove is donned on the hand, the microcapsules rupture. The ruptured microcapsules lubricate the glove and moisturize the hand to improve both wet and dry hand donnability. Microcapsules may be used in different amounts and with other materials to achieve the same or better results for increased donnability. The embodiments set forth in Tables 1-6 are not exhaustive and represent only a few possible combinations that include microcapsules to increase glove donnability.

TABLE 1

| Material | Test 1 | Test 2 |
|---|---|---|
| Water | 700.15 g | 3850.83 g |
| Polyurethane | 91.43 g | 502.86 g |
| Microcapsules | 8.42 g | 46.32 g |

One example of the polyurethane used according to the embodiments of the present invention set forth herein is Solucote 1088. Solucote 1088 is available from Soluol Chemical Company located in West Warwick, R.I. and will be used as but one example of a polyurethane that may be used according to the principles of the present invention, but is not limited thereto. Unless otherwise specified, the polyurethane used by the examples set forth herein according to the present invention is Solucote 1088.

One example of the microcapsules used according to the embodiments of the present invention set forth herein is LIPOCAPSULE™. LIPOCAPSULE™ is available from Lipo Technologies and will be used as an example of the microcapsules that may be used according to the principles of the present invention, but is not limited thereto. Unless otherwise specified, the microcapsules used in the examples of the present invention are LIPOCAPSULE™ made from Panalene®, vanilla fragrance, Vitamin A Palmitate and Vitamin E Acetate and having a microcapsule coating having a polyoxymethylene urea. Panalene® is hydrogenated polyisobutene, and is a registered mark of BP.

According to the present invention, polyurethane favorably binds microcapsules to the latex film of the glove. FIG. 1 illustrates a scanning electron photomicrograph of the microcapsules and shows their approximate measurements. The microcapsules comprise a core material and a microcapsule coating as set forth herein. The use of microcapsules having other core materials and microcapsule coatings may have varying results in the present invention, among them enhanced donnability, pleasant odor, and increased moisturizing properties.

The examples of the present invention shown in Tables 1-6 illustrate that the microcapsules tested bind well to latex with the use of polyurethane and enhance both damp and dry hand donning. Additional embodiments of the present invention may be used to achieve similar or better results by applying the microcapsules to the wet latex film of the glove, forming a compound with the microcapsules and the latex, or using the microcapsules in a slurry as a final dip.

Figure 10:
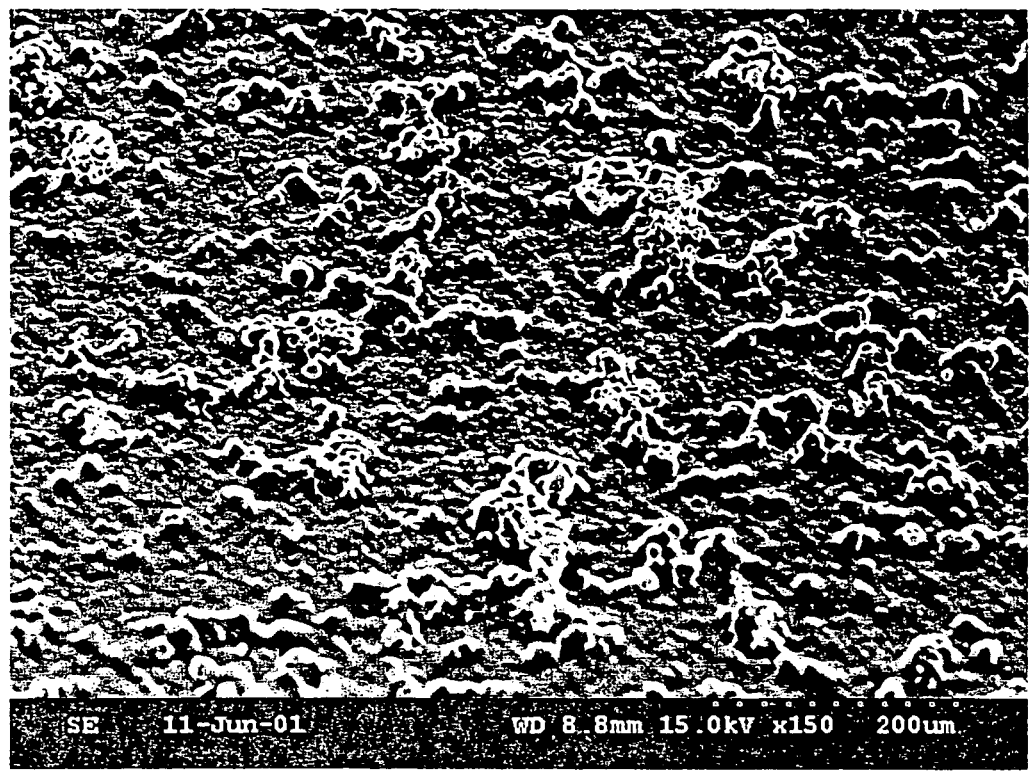
FIG. 10 is a scanning electron photomicrograph according to an embodiment of the present invention having a 1 weight % microcapsule overdip at a 0% stretch.
Figure 11:
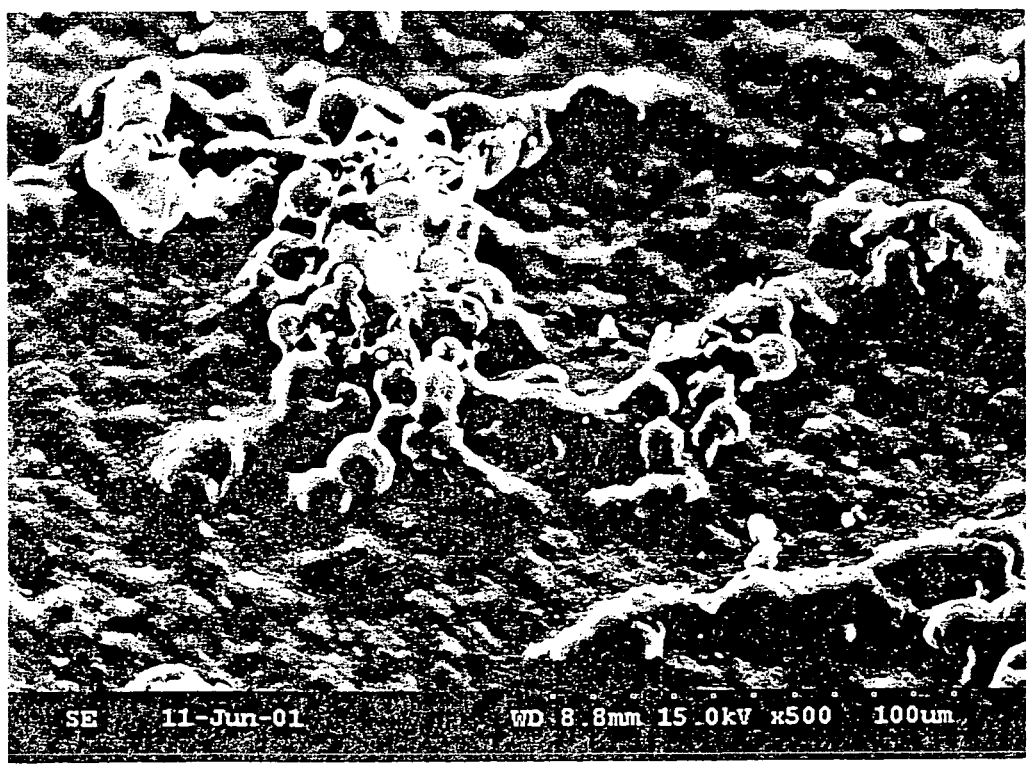
FIG. 11 is a scanning electron photomicrograph according to an embodiment of the present invention having a 1 weight % microcapsule overdip at a 0% stretch.

In one example of the present invention, the microcapsules are present in the overdip coating at a level of 1% by weight mixed with polyurethane and water. This embodiment, shown in Test 1 and in a larger batch as Test 2 in Table 1, was found to produce favorable results in dry donning tests and the polyurethane was found to bind the microcapsules well to the surface of the glove. FIGS. 2-9 show scanning electron photomicrographs of tube samples with a 1 weight % microcapsule overdip coating. FIGS. 10 and 11 illustrate scanning electron photomicrographs of sample gloves with a 1 weight % microcapsule overdip coating.

Figure 12:
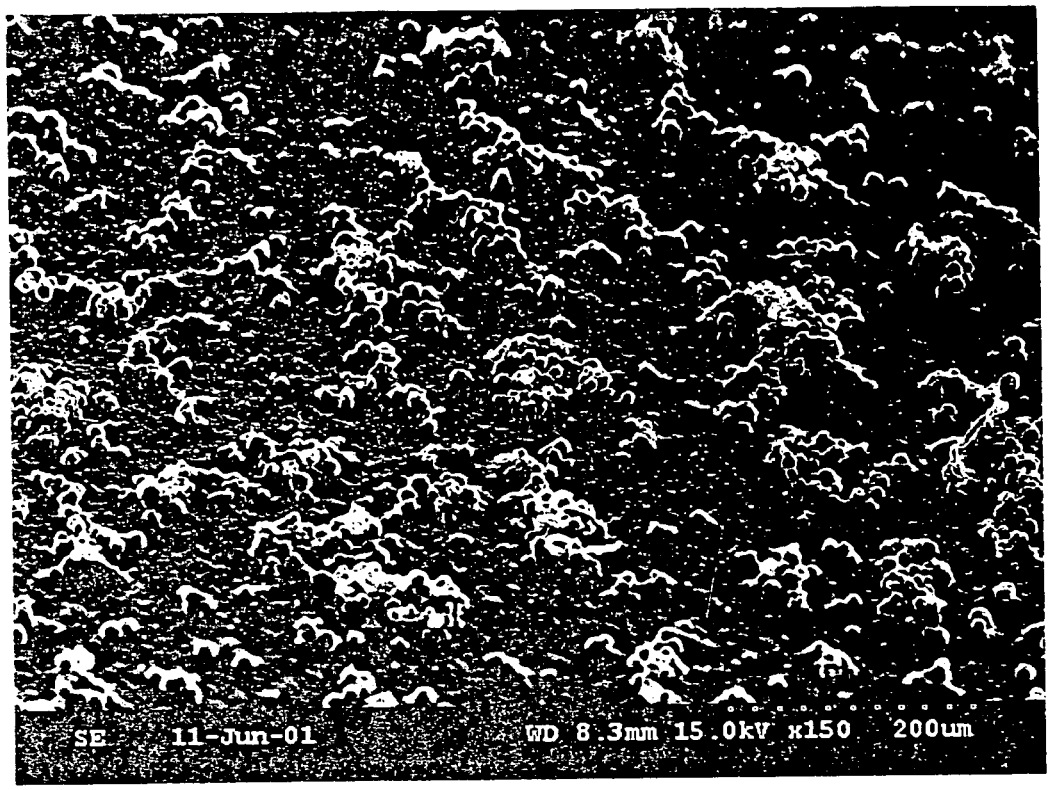
FIG. 12 is a scanning electron photomicrograph according to an embodiment of the present invention having a 2 weight % microcapsule overdip at a 0% stretch.
Figure 13:
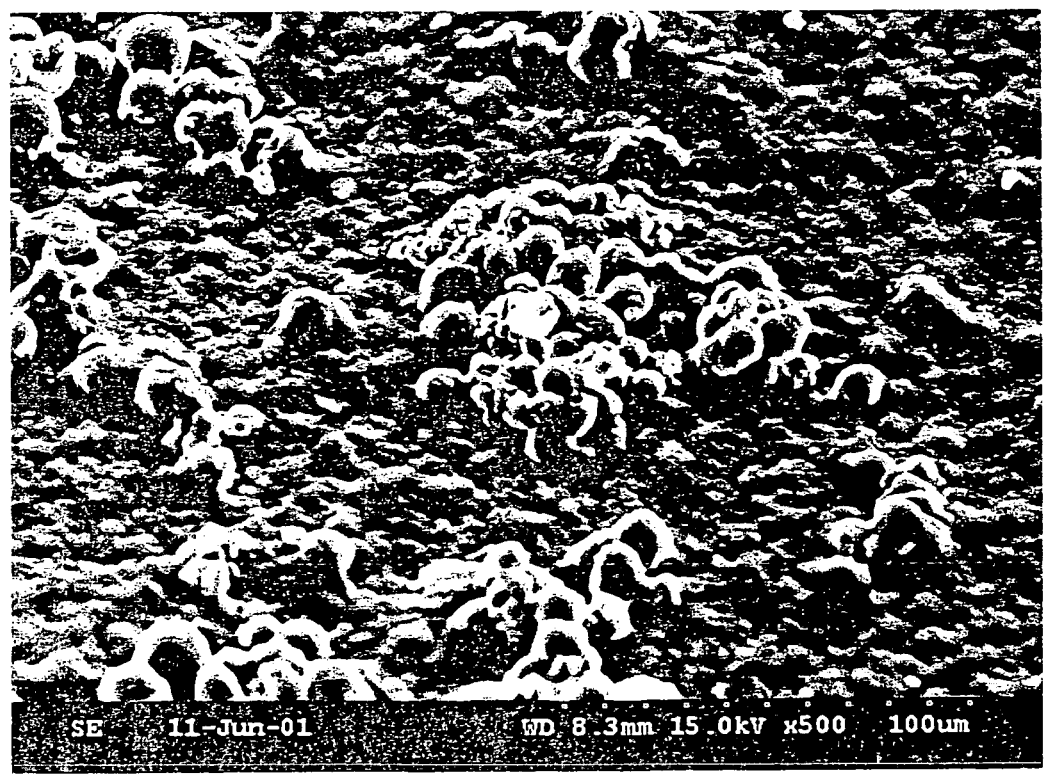
FIG. 13 is a scanning electron photomicrograph according to an embodiment of the present invention having a 2 weight % microcapsule overdip at a 0% stretch.
Figure 14:
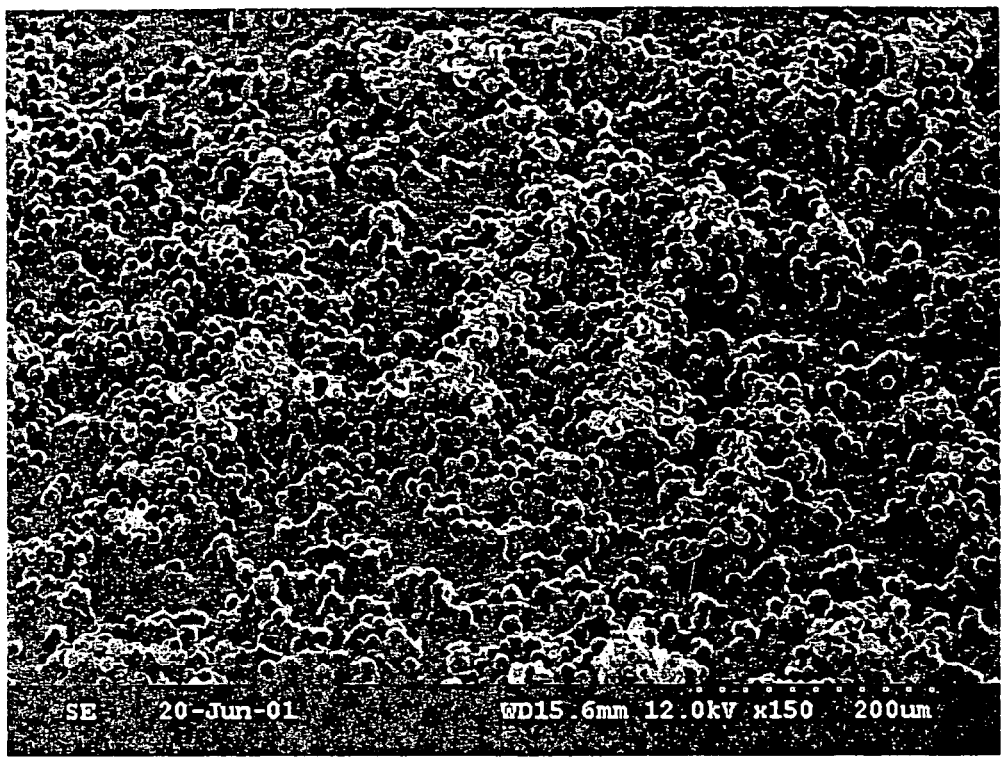
FIG. 14 is a scanning electron photomicrograph according to an embodiment of the present invention having a 1.75 weight % microcapsule overdip at a 0% stretch.
Figure 15:
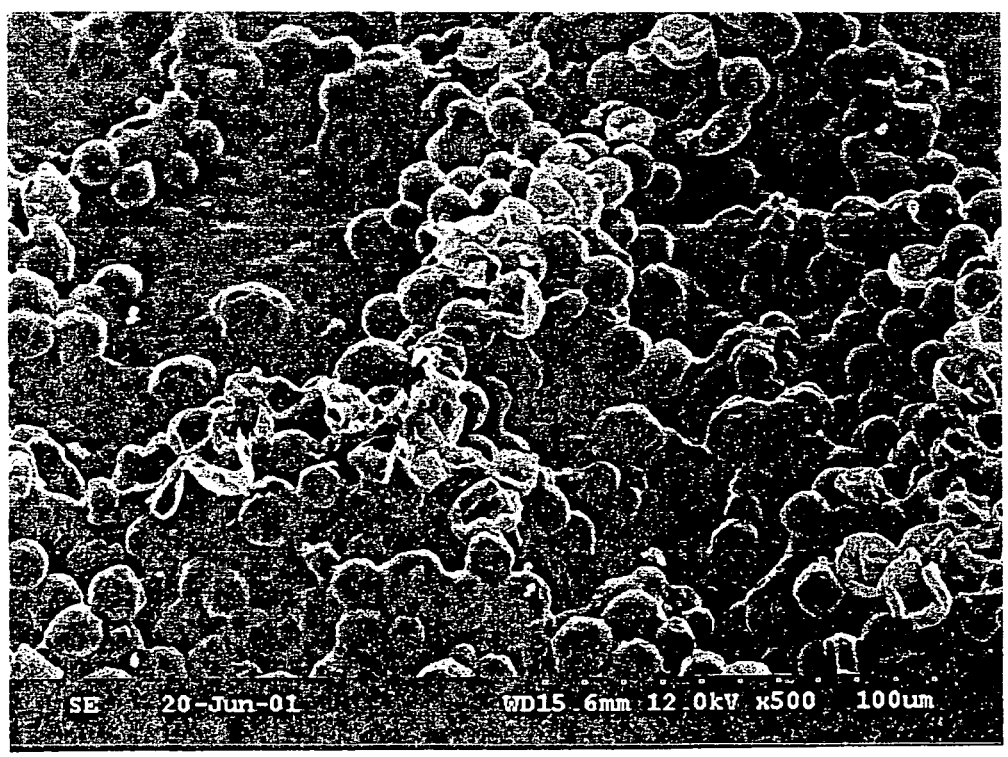
FIG. 15 is a scanning electron photomicrograph according to an embodiment of the present invention having a 1.75 weight % microcapsule overdip at a 0% stretch.
Figure 16:
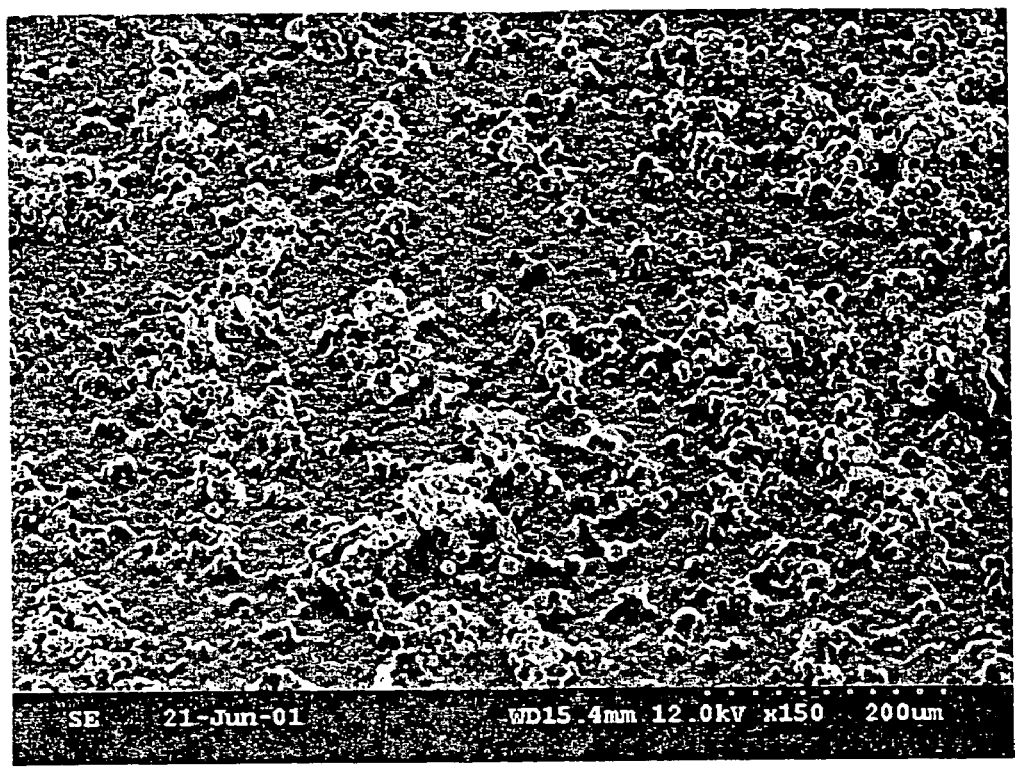
FIG. 16 is a scanning electron photomicrograph according to an embodiment of the present invention having a 1.75 weight % microcapsule overdip at a 500% stretch.
Figure 17:
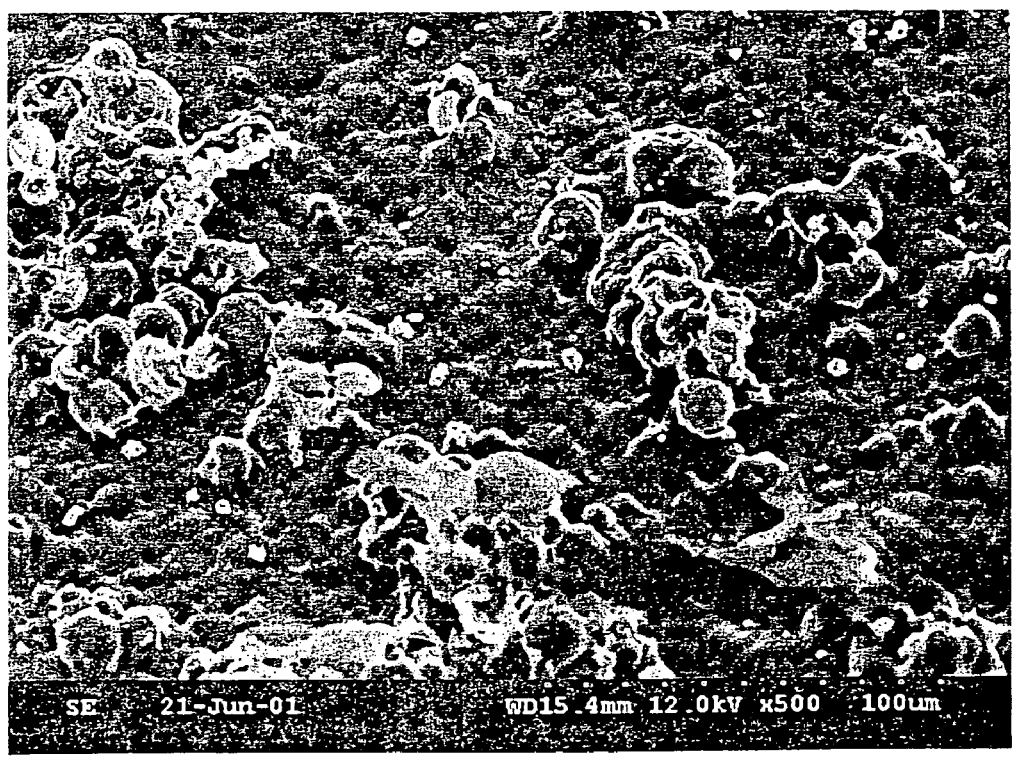
FIG. 17 is a scanning electron photomicrograph according to an embodiment of the present invention having a 1.75 weight % microcapsule overdip at a 500% stretch.
Figure 18:
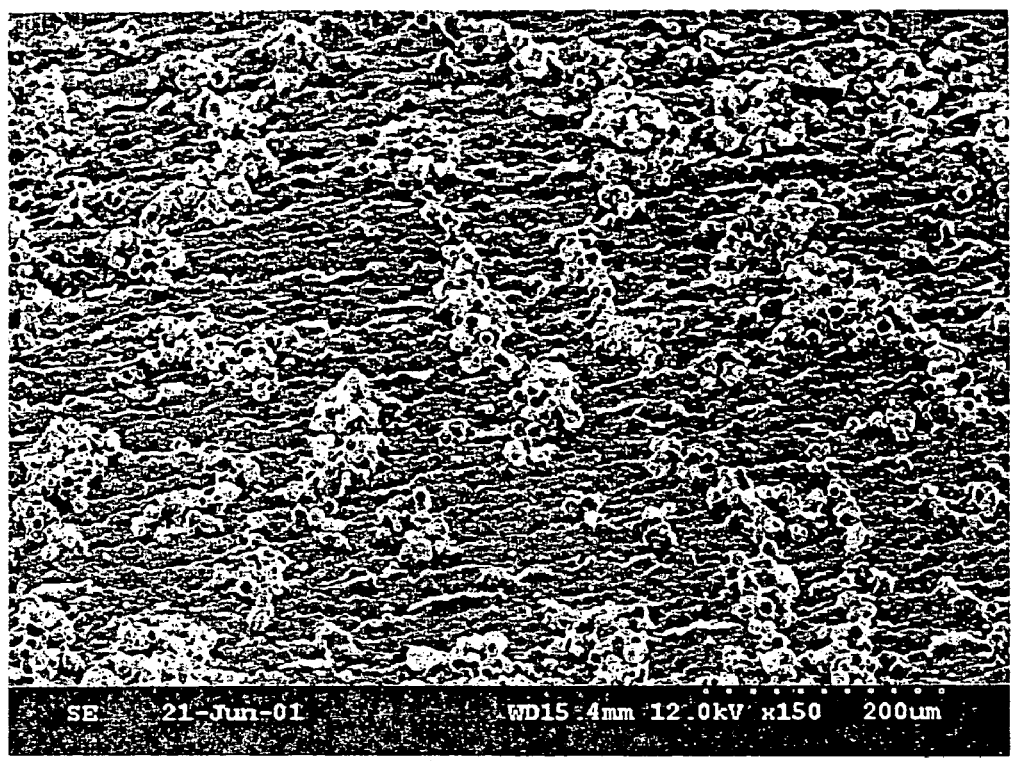
FIG. 18 is a scanning electron photomicrograph according to an embodiment of the present invention having a 1.75 weight % microcapsule overdip at a 5×700% stretch.
Figure 19:
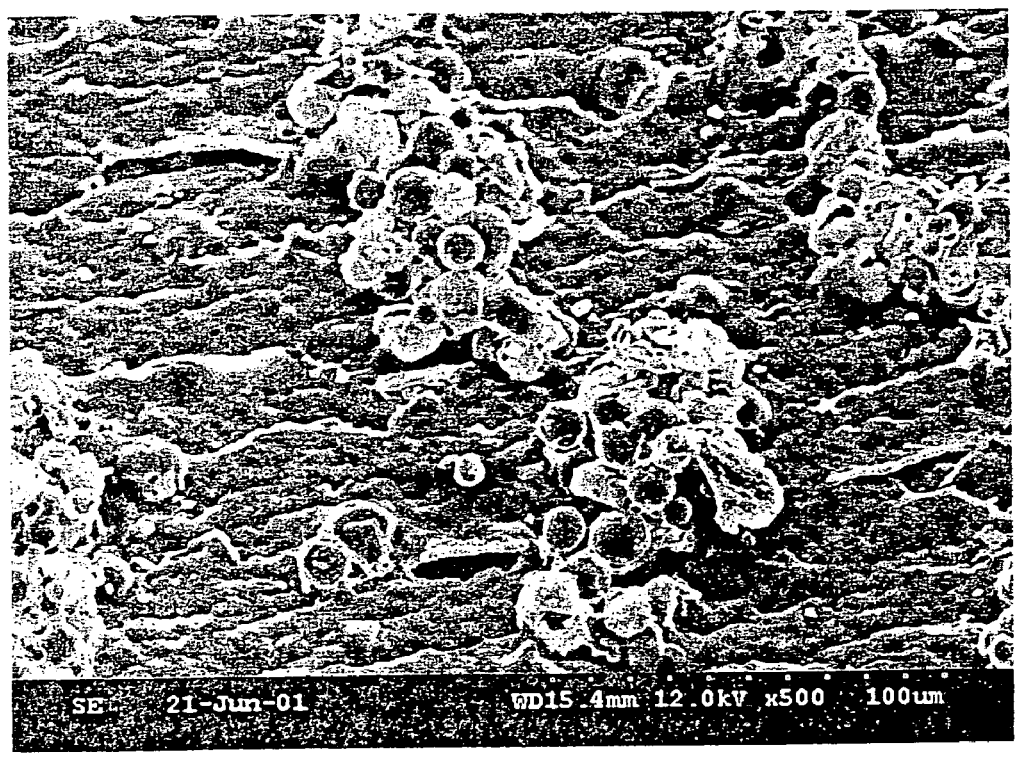
FIG. 19 is a scanning electron photomicrograph according to an embodiment of the present invention having a 1.75 weight % microcapsule overdip at a 5×700% stretch.
Figure 20:
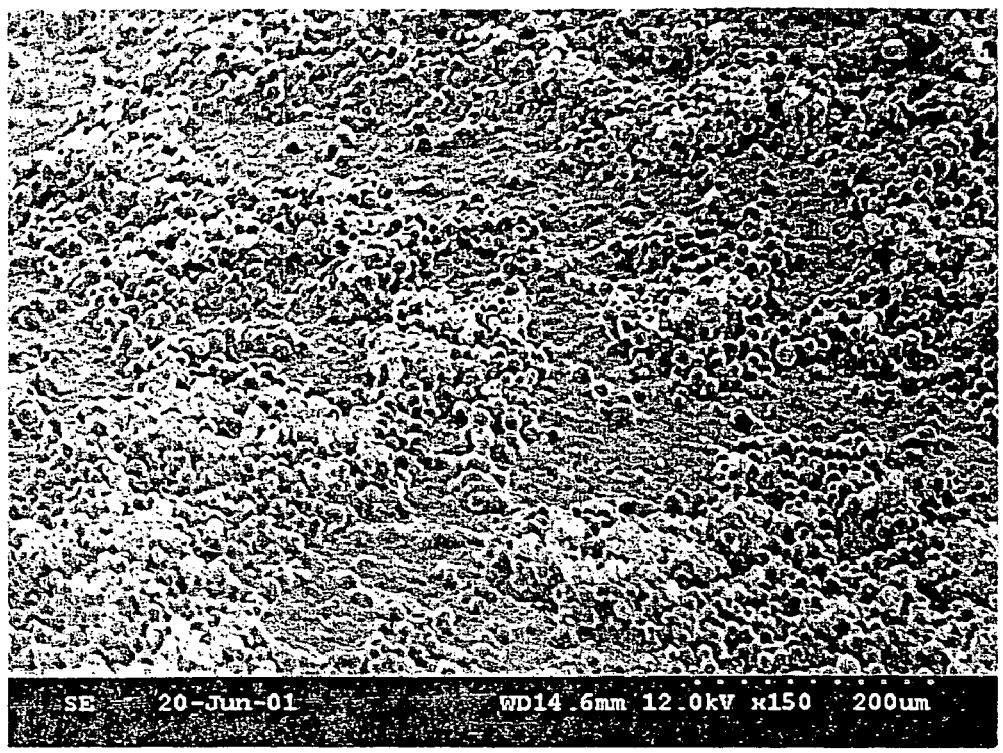
FIG. 20 is a scanning electron photomicrograph according to an embodiment of the present invention having a 1.5 weight % microcapsule overdip at a 0% stretch.
Figure 21:
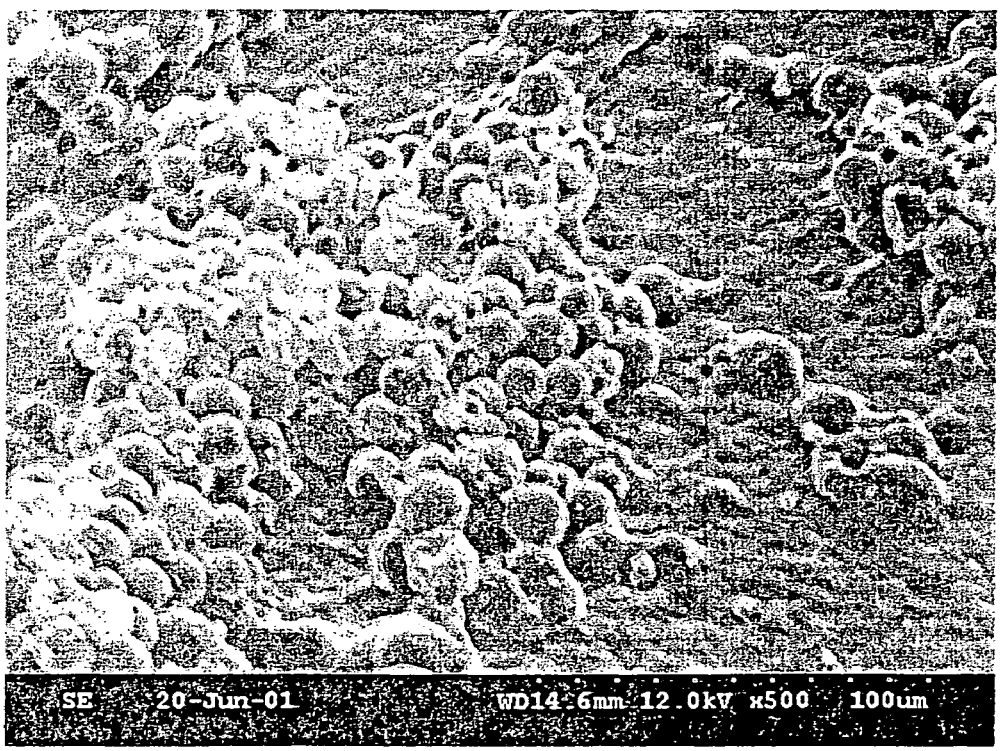
FIG. 21 is a scanning electron photomicrograph according to an embodiment of the present invention having a 1.5 weight % microcapsule overdip at a 0% stretch.
Figure 22:
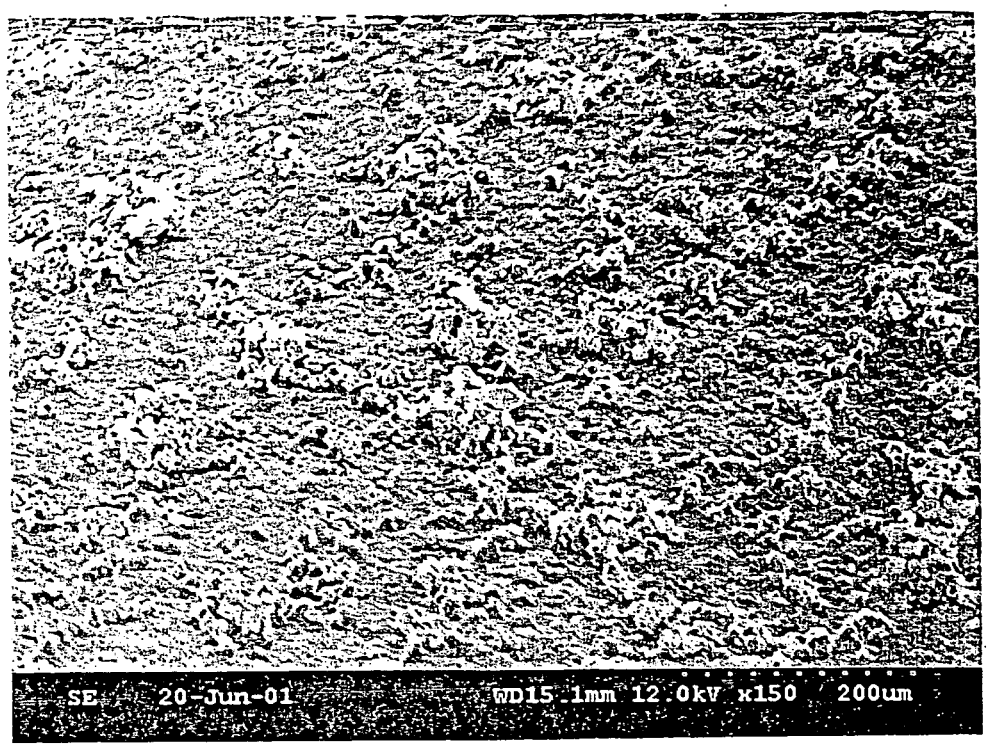
FIG. 22 is a scanning electron photomicrograph according to an embodiment of the present invention having a 1.5 weight % microcapsule overdip at a 500% stretch.
Figure 23:
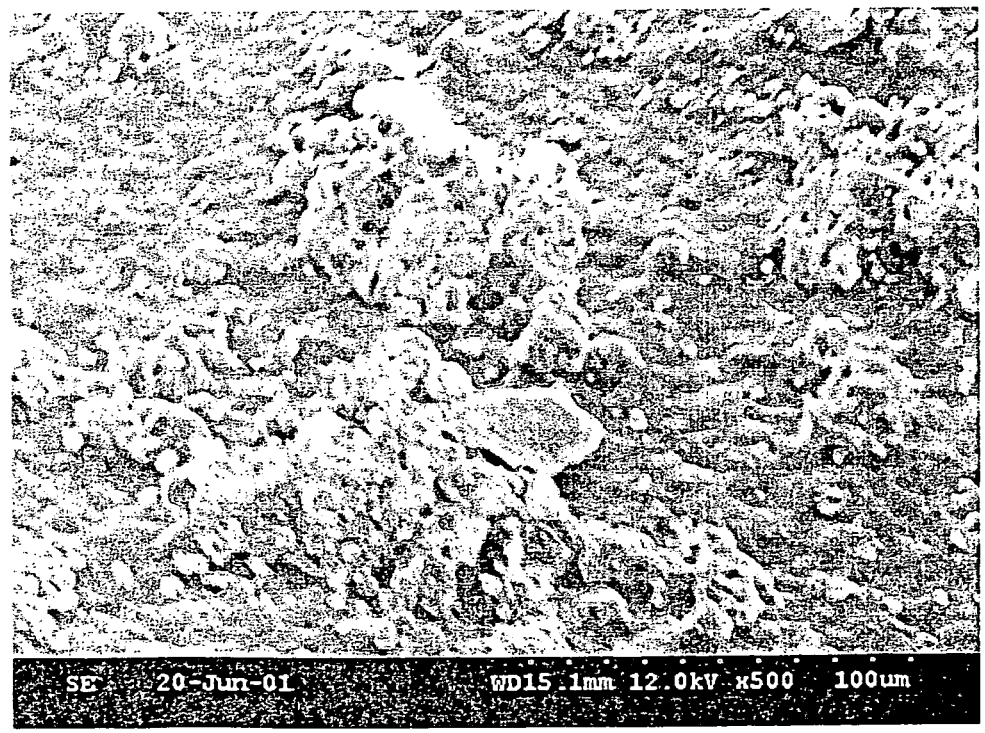
FIG. 23 is a scanning electron photomicrograph according to an embodiment of the present invention having a 1.5 weight % microcapsule overdip at a 500% stretch.
Figure 24:
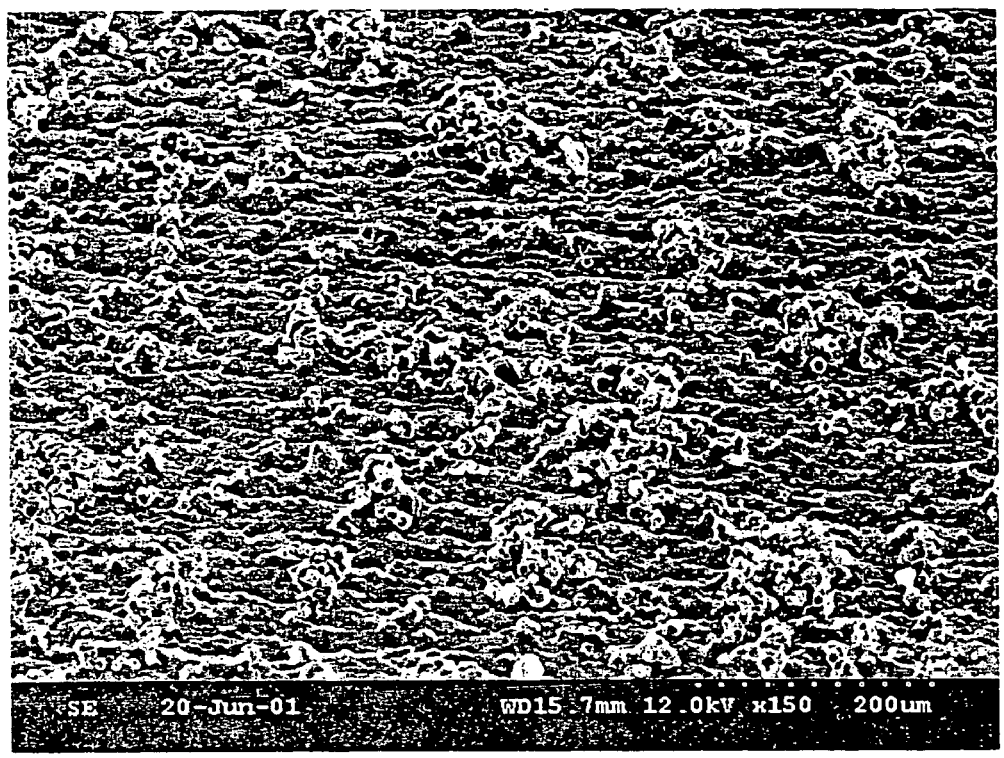
FIG. 24 is a scanning electron photomicrograph according to an embodiment of the present invention having a 1.5 weight % microcapsule overdip at a 5×700% stretch.
Figure 25:
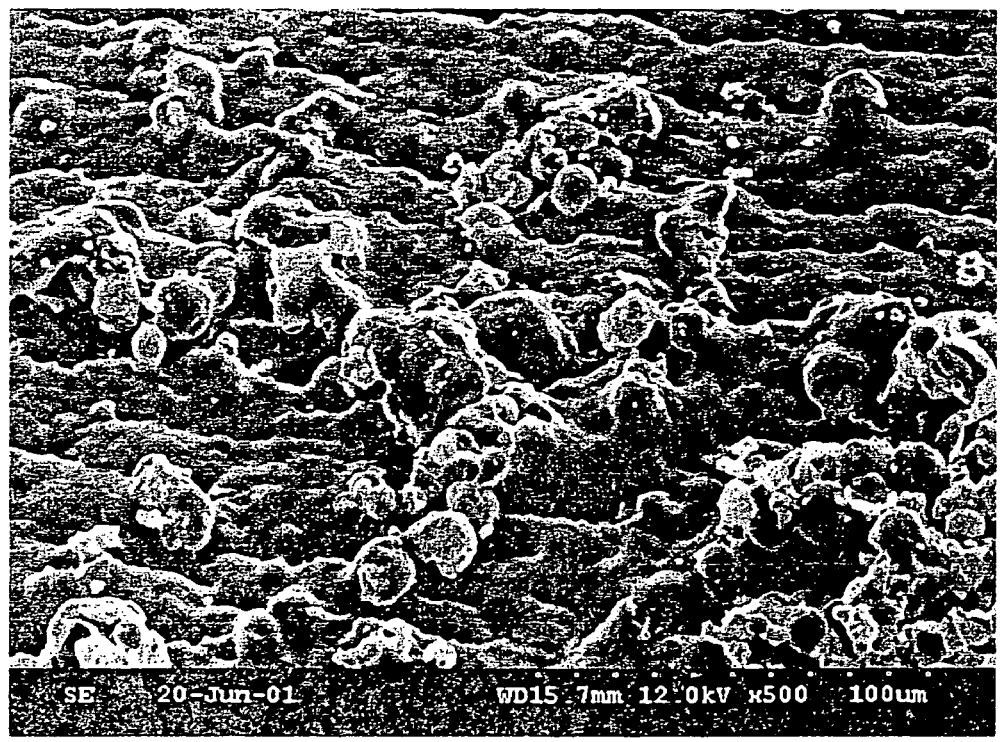
FIG. 25 is a scanning electron photomicrograph according to an embodiment of the present invention having a 1.5 weight % microcapsule overdip at a 5×700% stretch.
Figure 26:
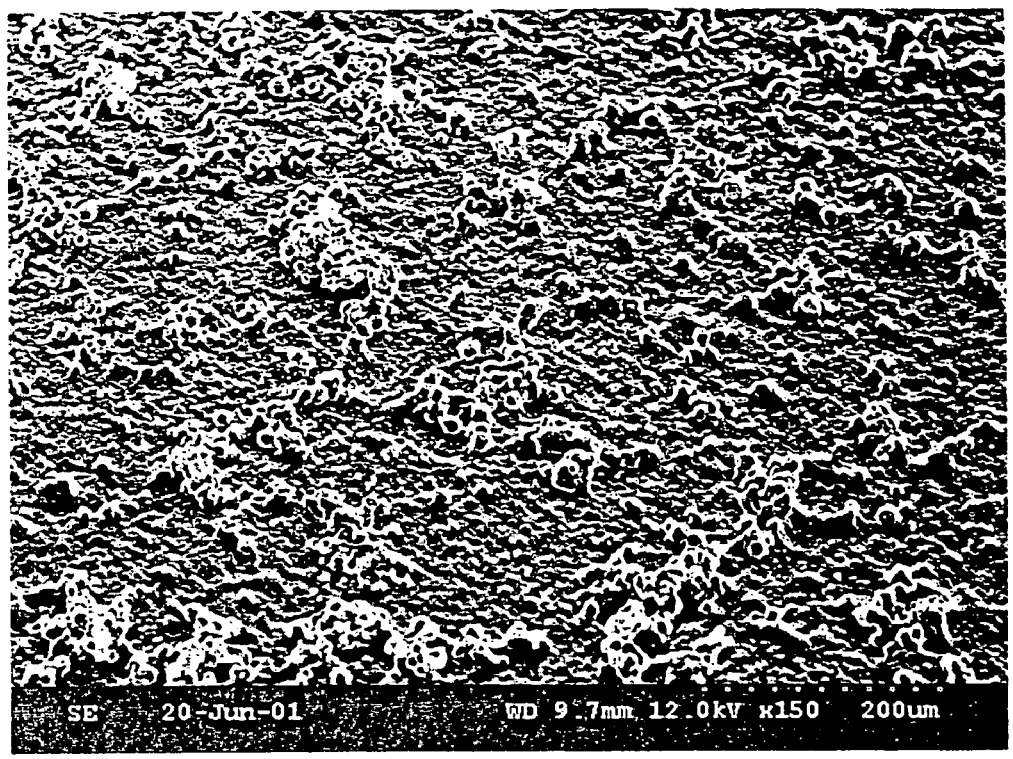
FIG. 26 is a scanning electron photomicrograph according to an embodiment of the present invention having a 1.25 weight % microcapsule overdip at a 0% stretch.
Figure 27:
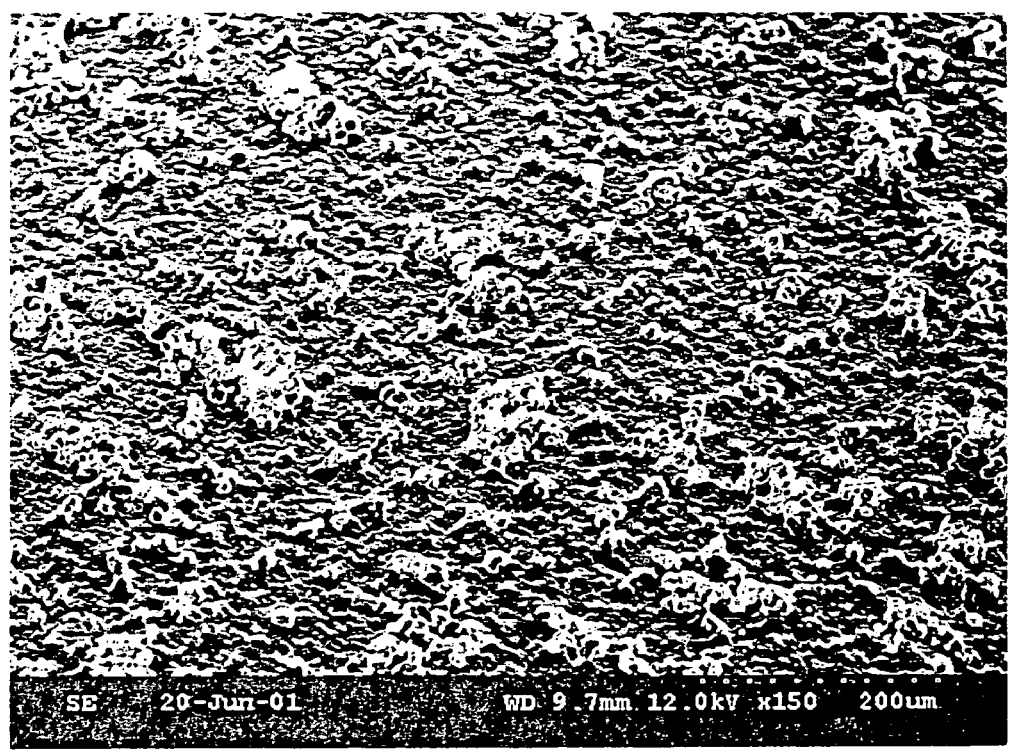
FIG. 27 is a scanning electron photomicrograph according to an embodiment of the present invention having a 1.25 weight % microcapsule overdip at a 500% stretch.
Figure 28:
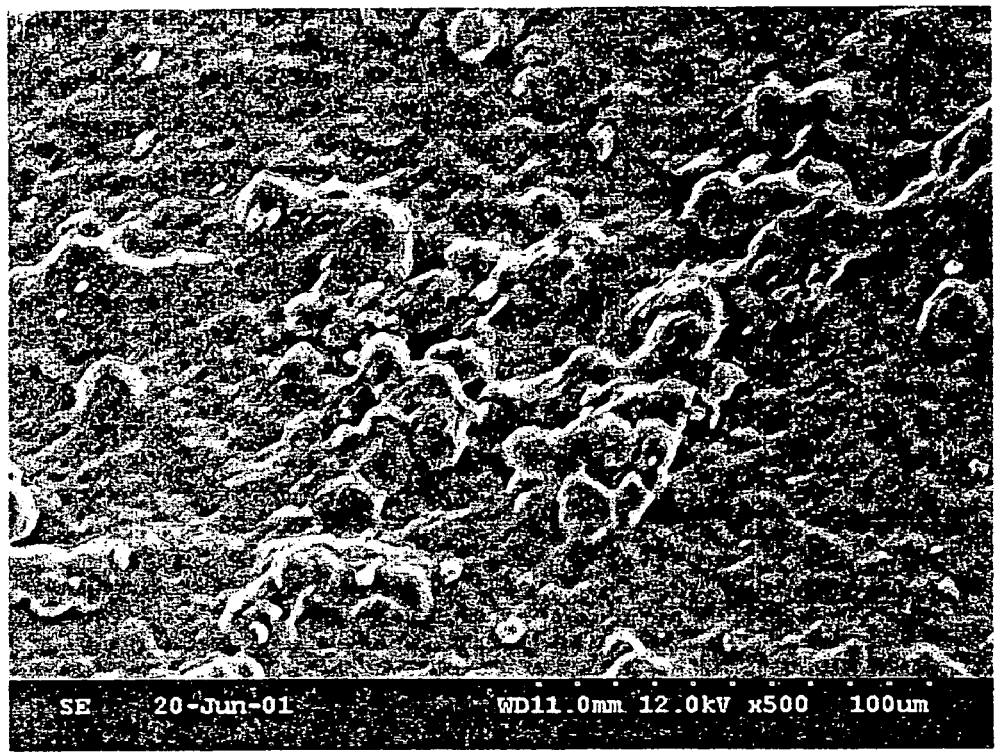
FIG. 28 is a scanning electron photomicrograph according to an embodiment of the present invention having a 1.25 weight % microcapsule overdip at a 0% stretch.
Figure 29:
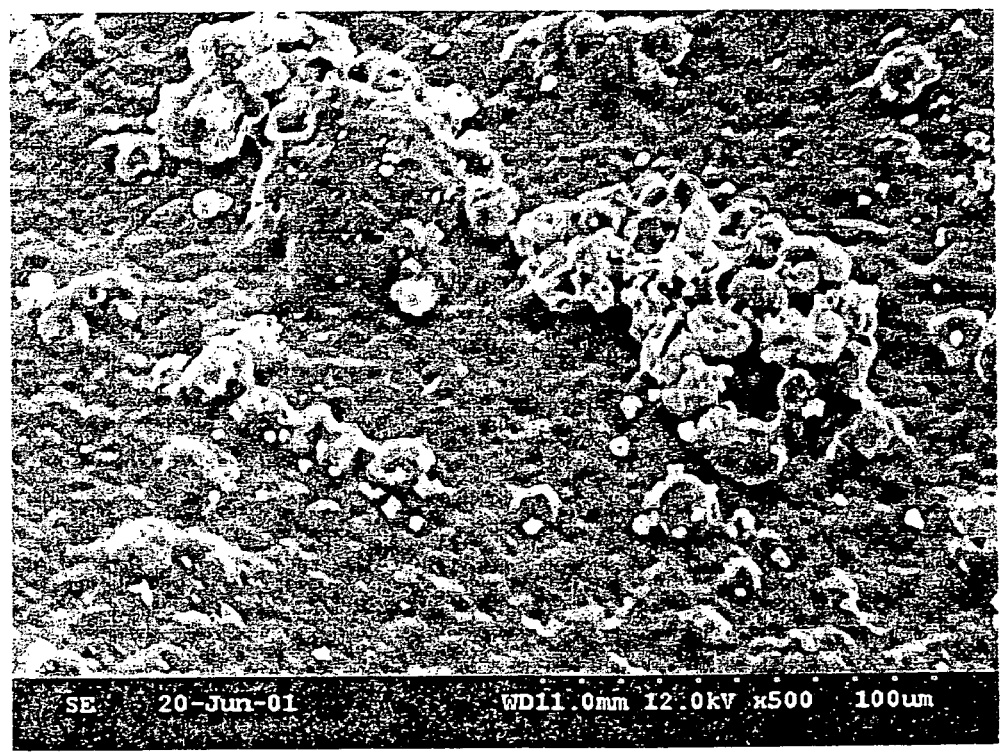
FIG. 29 is a scanning electron photomicrograph according to an embodiment of the present invention having a 1.25 weight % microcapsule overdip at a 500% stretch.
Figure 30:
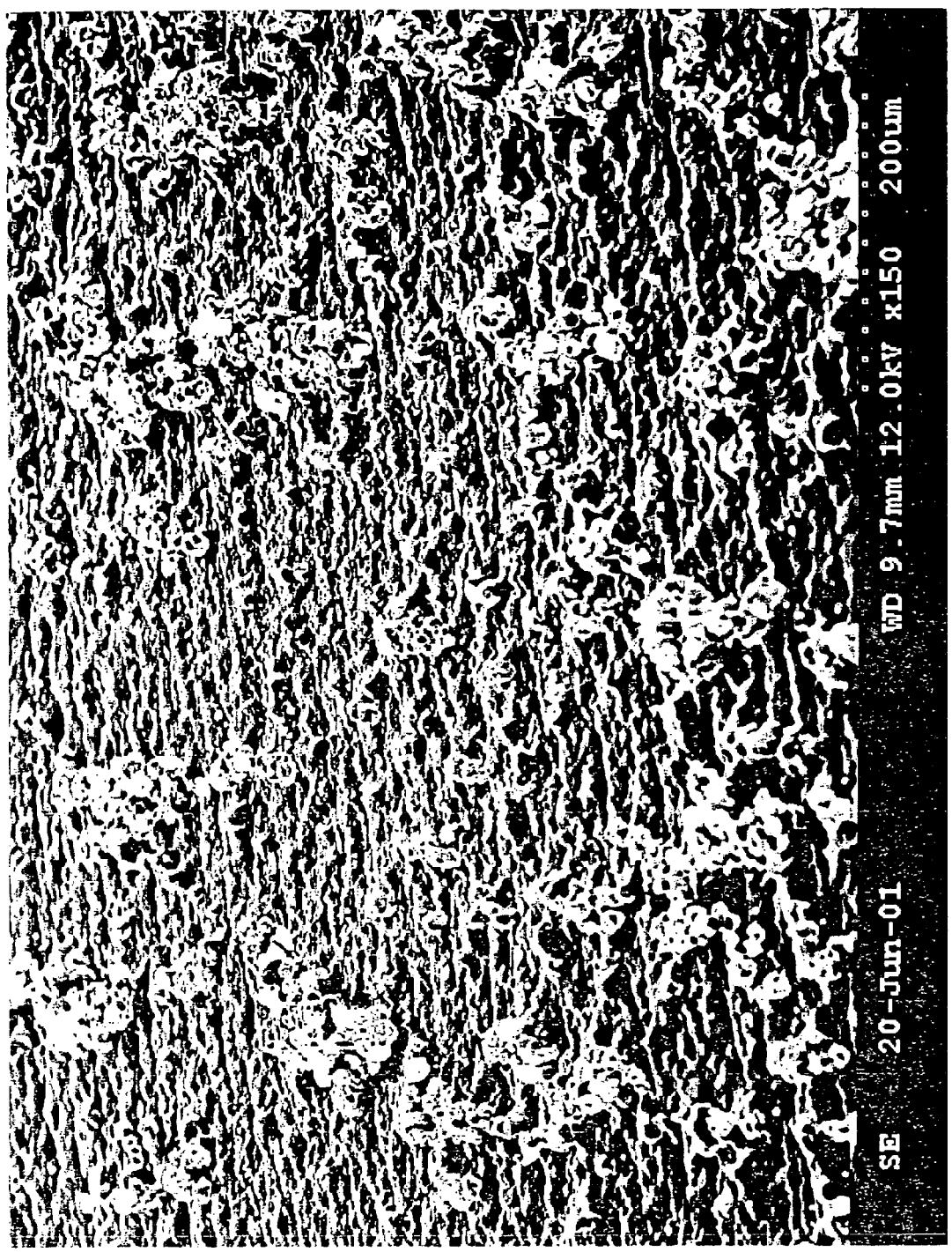
FIG. 30 is a scanning electron photomicrograph according to an embodiment of the present invention having a 1.25 weight % microcapsule overdip at a 5×700% stretch.
Figure 31:
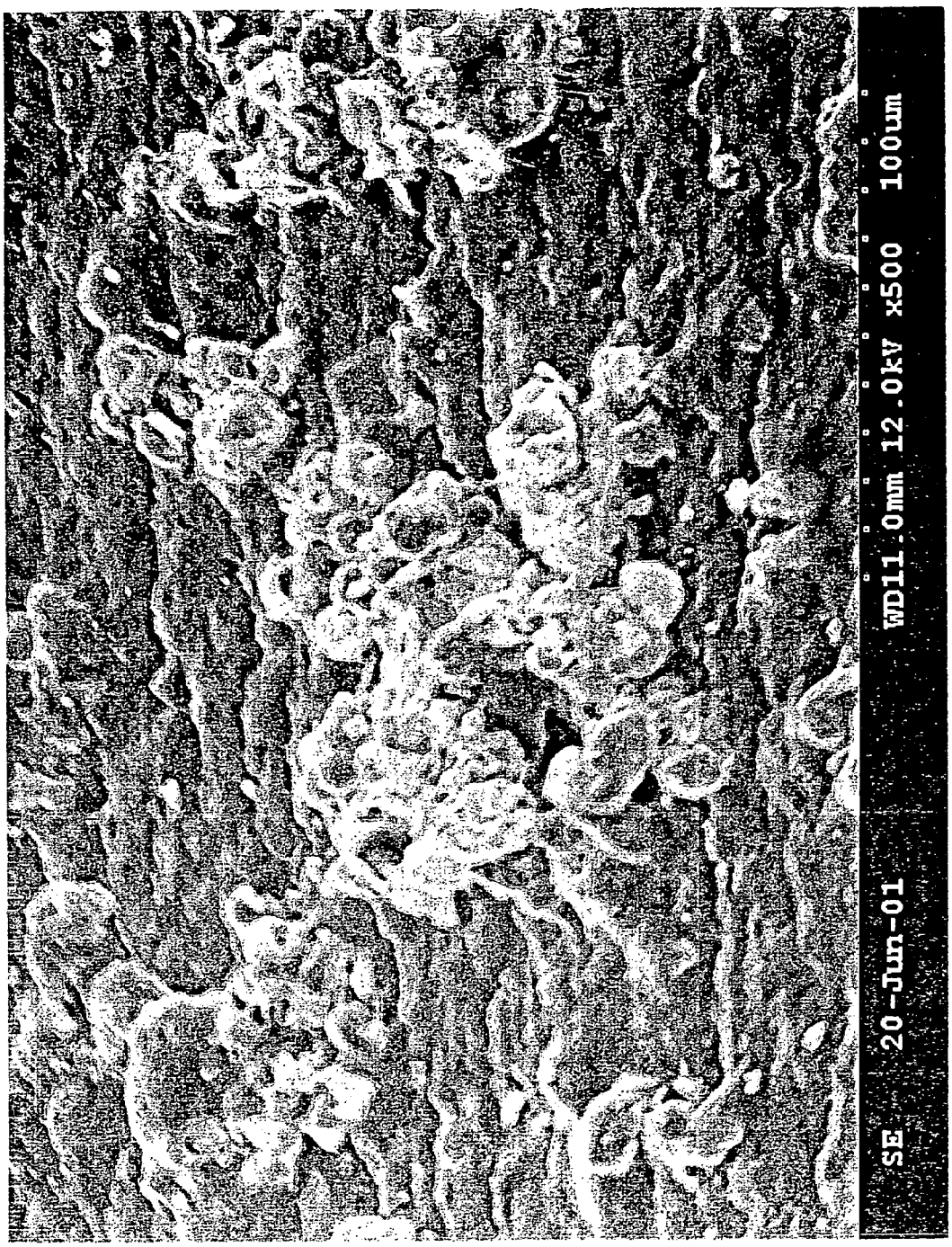
FIG. 31 is a scanning electron photomicrograph according to an embodiment of the present invention having a 1.25 weight % microcapsule overdip at a 5×700% stretch.
Figure 32:
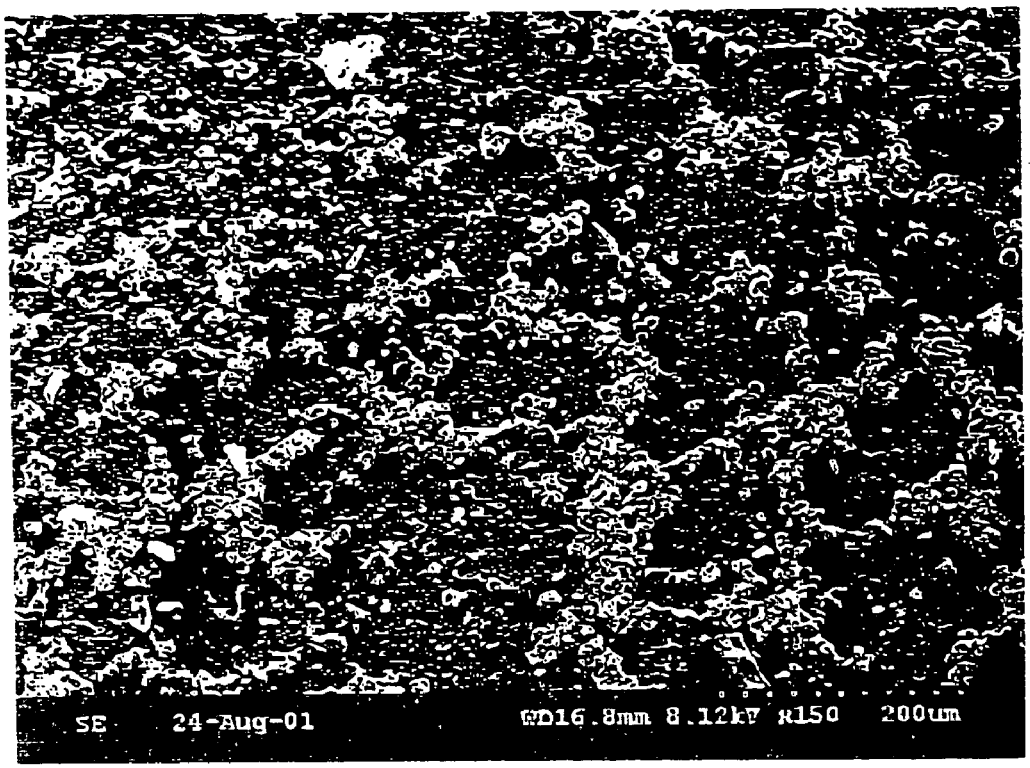
FIG. 32 is a scanning electron photomicrograph of a tube sample having a 4 weight % microcapsule overdip at a 0% stretch according to the present invention.
Figure 33:
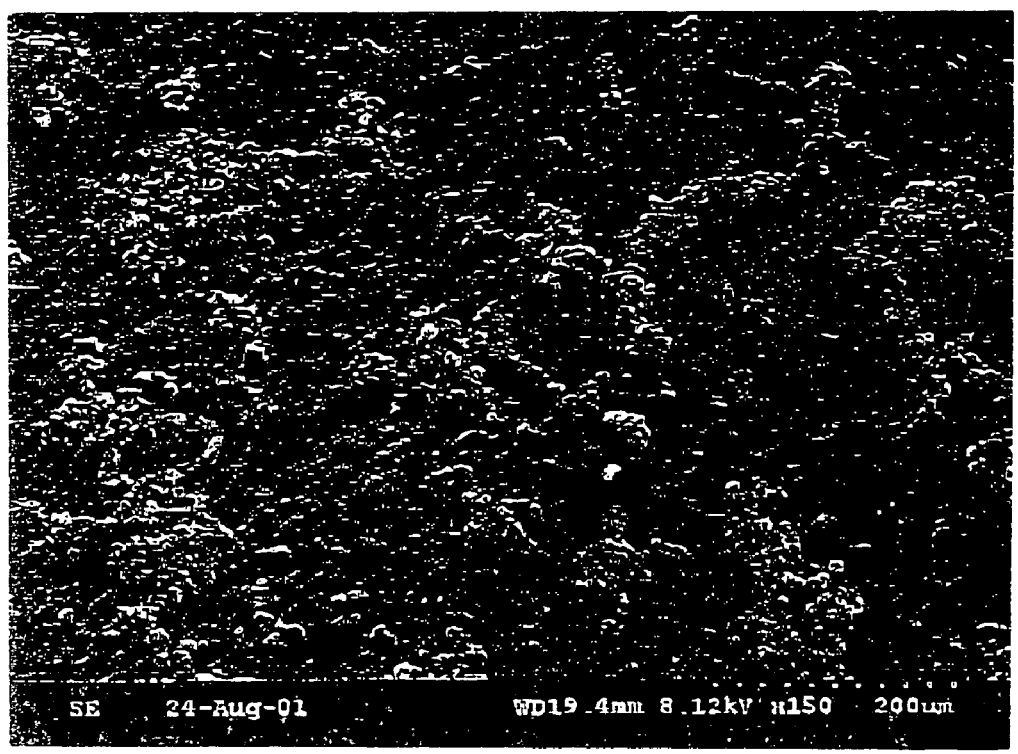
FIG. 33 is a scanning electron photomicrograph of a tube sample having a 4 weight % microcapsule overdip at a 500% stretch according to the present invention.
Figure 34:
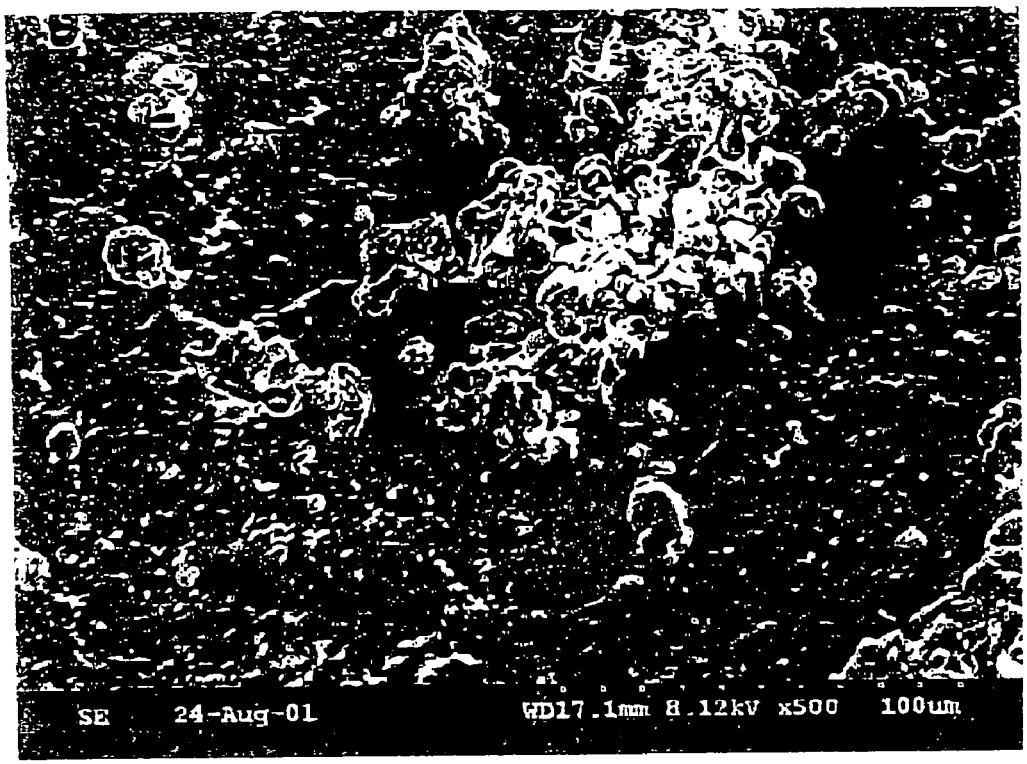
FIG. 34 is a scanning electron photomicrograph of a tube sample having a 4 weight % microcapsule overdip at a 0% stretch according to the present invention.
Figure 35:
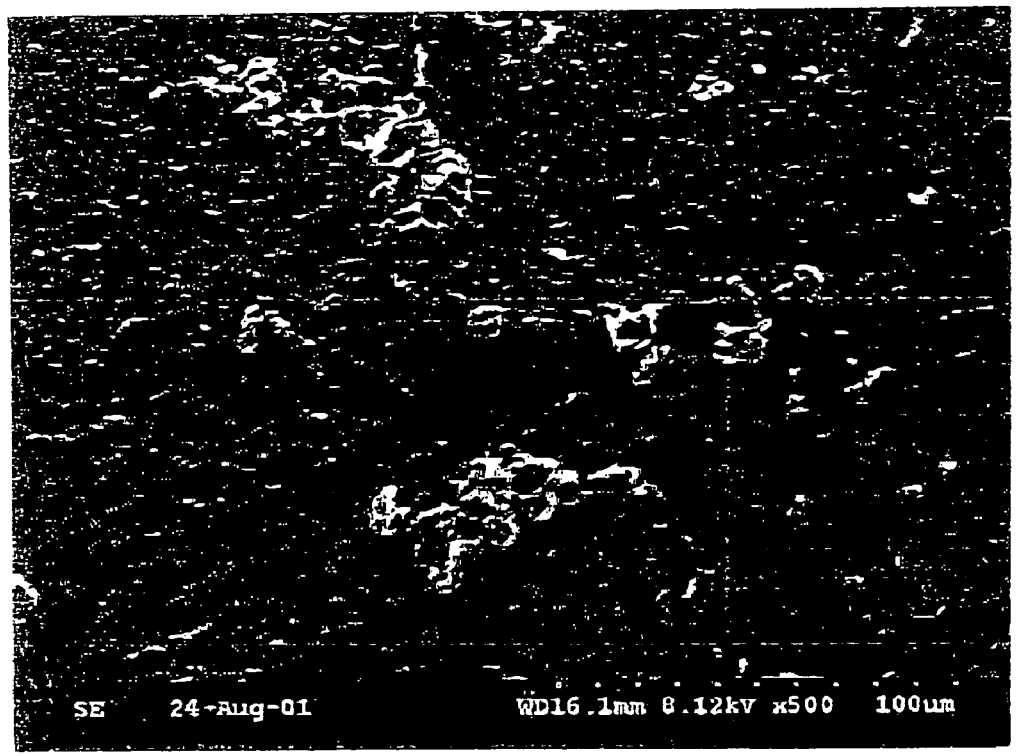
FIG. 35 is a scanning electron photomicrograph of a tube sample having a 4 weight % microcapsule overdip at a 500% stretch according to the present invention.
Figure 36:
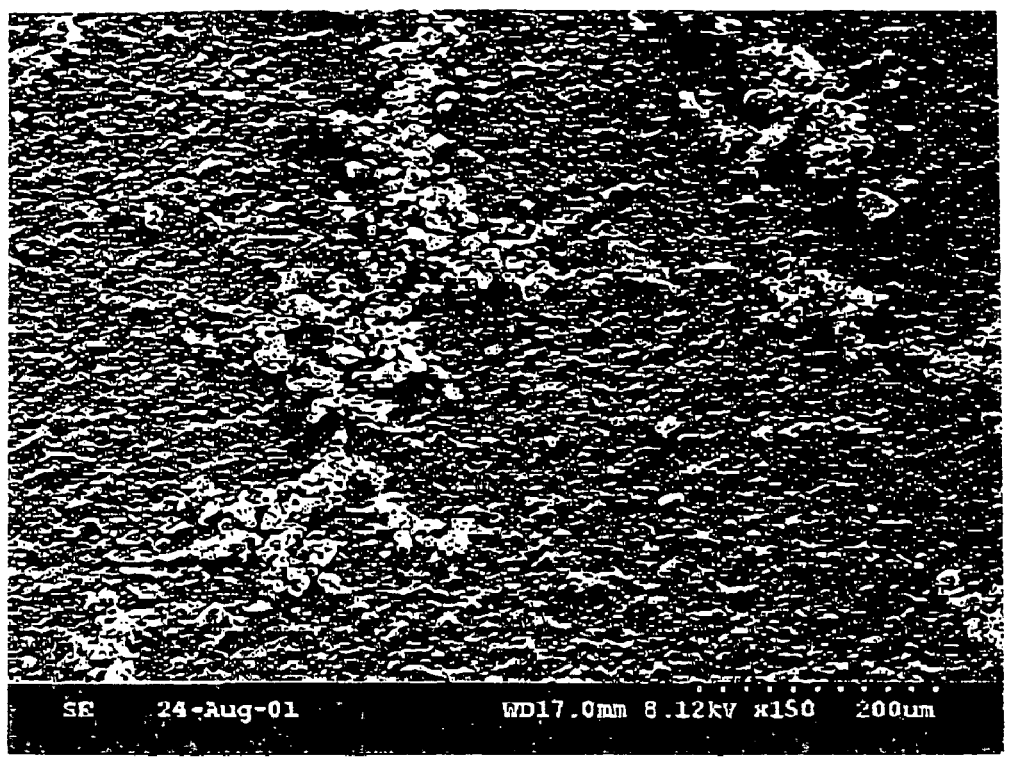
FIG. 36 is a scanning electron photomicrograph of a tube sample having a 4 weight % microcapsule overdip at a 5×700% stretch according to the present invention.
Figure 37:
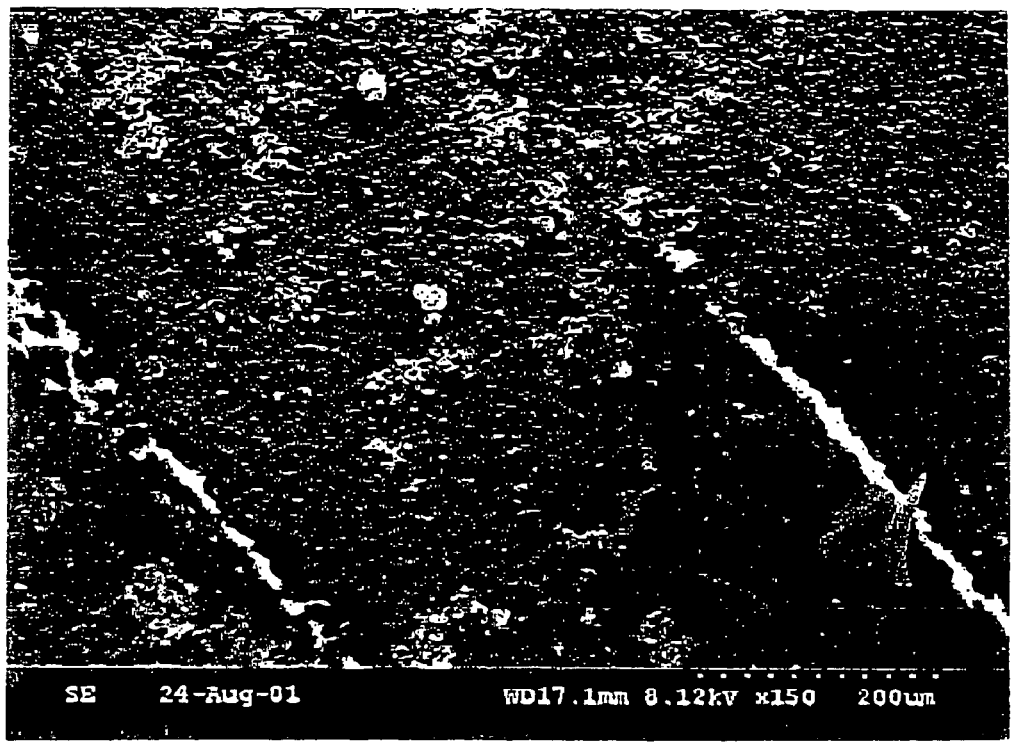
FIG. 37 is a scanning electron photomicrograph of a tube sample having a 4 weight % microcapsule overdip after a break according to the present invention.
Figure 38:
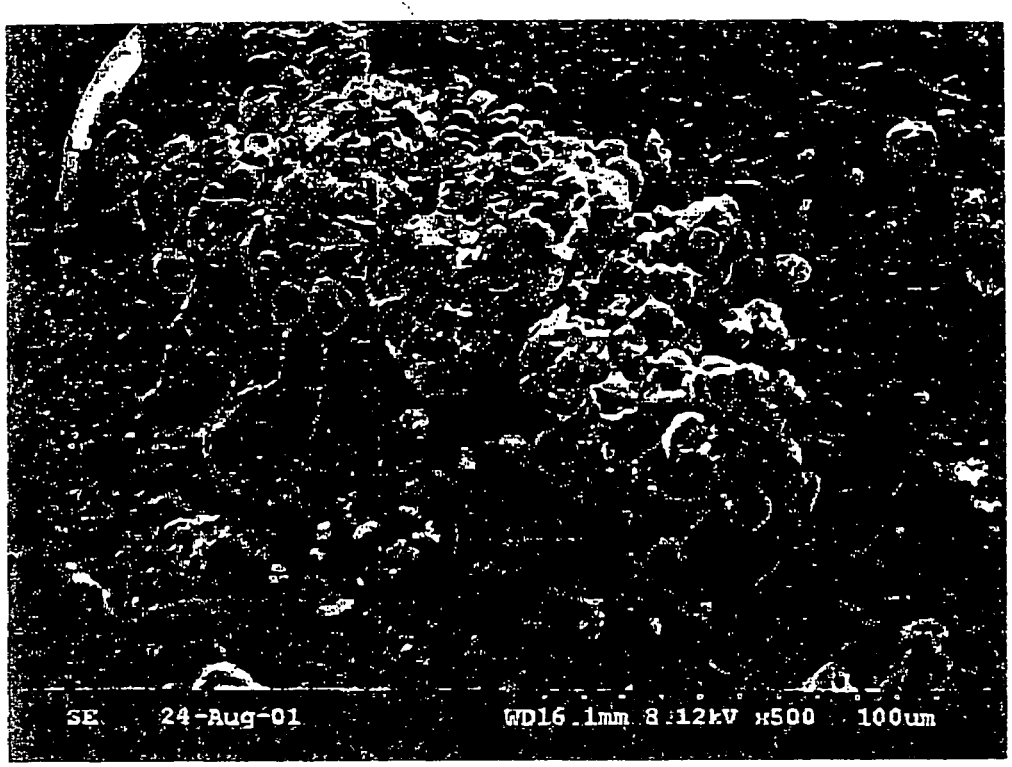
FIG. 38 is a scanning electron photomicrograph of a tube sample having a 4 weight % microcapsule overdip at a 5×700% stretch according to the present invention.
Figure 39:
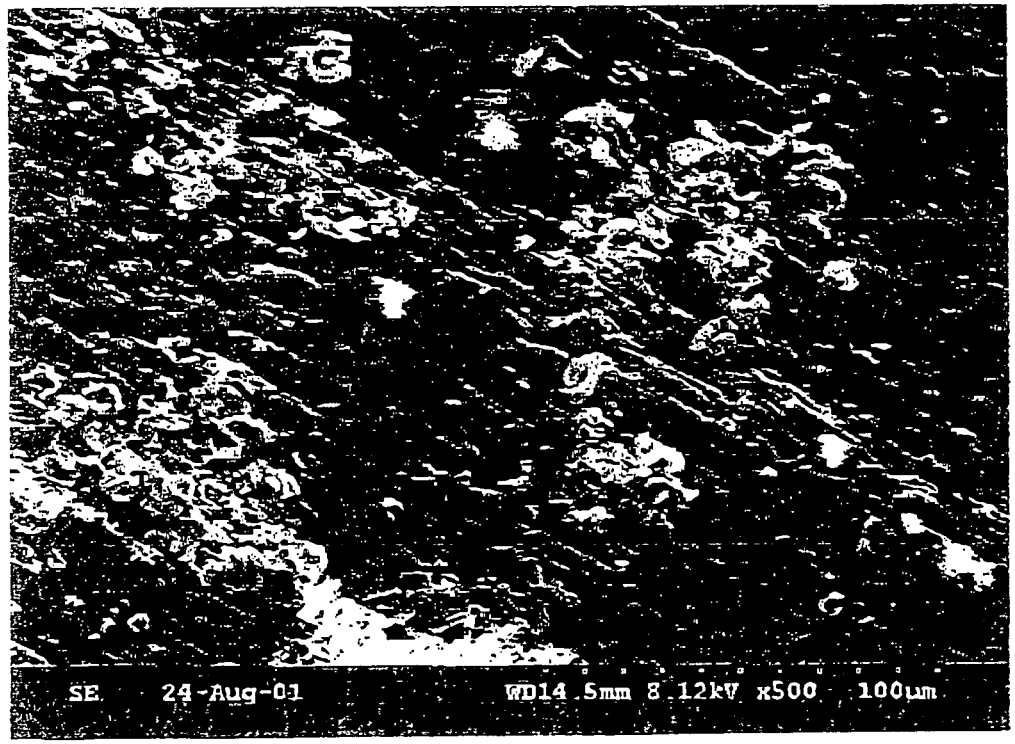
FIG. 39 is a scanning electron photomicrograph of a tube sample having a 4 weight % microcapsule overdip after a break according to the present invention.

In another example of the invention, a 2 weight % microcapsule overdip coating was created. The 2 weight % microcapsule overdip coating is illustrated in Table 2 below. In this example, the microcapsules were combined with polyurethane in water to make an overdip mix and applied to the glove. After the overdip coating was applied, the surface of the glove displayed some particulate matter. FIGS. 12 and 13 illustrate scanning electron photomicrographs of glove surfaces with the 2 weight % microcapsule overdip.

TABLE 2

| Material | Test 3 |
|---|---|
| Water | 3850.83 g |
| Polyurethane | 502.86 g |
| Microcapsules | 92.64 g |

In another example of the present invention, the microcapsule overdip includes a 1.75 weight % microcapsule overdip with polyurethane and water. FIGS. 14-19 represent scanning electron photomicrographs of gloves with the 1.75 weight % microcapsule overdip. Table 3 shows the ratio of materials used in the 1.75 weight % microcapsule overdip coating. The 1.75 weight % microcapsule overdip coating was found to have increased donning capabilities as well as moisturizing properties and a fragrant scent.

TABLE 3

| Material | Test 4 |
|---|---|
| Water | 4,361.62 g |
| Polyurethane | 574.74 g |
| Microcapsules | 92.64 g |

Another example of the present invention includes an overdip comprising 1.5 weight % microcapsules, polyurethane and water. The 1.5 weight % microcapsule overdip coating is represented by Table 4. FIGS. 20-25 show scanning electron photomicrographs of gloves with the 1.5 weight % microcapsule overdip. The 1.5 weight % microcapsule overdip, as illustrated also facilitates donning of the gloves on both damp and dry hands while maintaining a pleasant odor and moisturizing the hands.

TABLE 4

| Material | Test 5 |
|---|---|
| Water | 5,103.85 g |
| Polyurethane | 670.51 g |
| Microcapsules | 92.64 g |

A further example of the present invention includes an overdip coating solution comprising a 1.25 weight % microcapsule, water and polyurethane. Table 5 shows the components of the 1.25 weight % microcapsule overdip coating formulation. FIGS. 26-31 illustrate scanning electron photomicrographs of gloves with the 1.25 weight % microcapsule overdip. The 1.25 weight % microcapsule overdip coating has proven to increase donning capabilities for both damp and dry hands. It also showed improved fragrance and moisturizing properties as well.

TABLE 5

| Material | Test 6 |
|---|---|
| Water | 6,143.67 g |
| Polyurethane | 804.69 g |
| Microcapsules | 92.64 g |

Another example of the present invention has about a 4 weight % microcapsule overdip with water and polyurethane. Table 6 shows the components of the overdip solution for this embodiment. FIGS. 32-39 illustrate scanning electron photomicrographs of tube samples with the 4 weight % overdip solution. This example also shows increased donning capabilities for both damp and dry hands and adheres well to the rubber layer.

TABLE 6

| Material | Test 7 |
|---|---|
| Water | 722.29 g |
| Polyurethane | 45.71 g |
| Microcapsules | 32.00 g |

The glove coatings with percentages of microcapsules falling between about 1 weight % and about 1 weight % as shown in Tables 1-6, proved to increase the donning capabilities of gloves in both dry and wet donning tests. The ratios provided in Tables 1-6 are illustrative of but a few examples of the embodiment of the present invention. The microcapsules, polyurethane and water may be used in varying proportions to achieve similar or better results. However, according to the principles of the present invention, a concentration of microcapsules from about 1 weight % to about 5 weight % based on the total weight of the glove coating may be used in making the coating.

The examples of the present invention as shown in Tables 1-6 also maintain a powder-free surface after manufacture of the glove is complete. Gloves made with the microcapsule overdips listed in Tables 1-6 exhibit very low levels of powder, less than 2 milligrams per glove, as shown in Table 7 after curing of the glove. The levels of powder exhibited by the examples of the present invention are significantly less than those typically found in standard gloves. Consistent with FDA regulations, the powder levels of a standard powder free glove are less than 2 mg while powdered gloves may have about 200 mg of powder per glove.

TABLE 7

| Percentage of Microcapsule (wt) | Powder Weight (in mg/glove) |
|---|---|
| 1.75% | 1.42 |
| 1.50% | 0.76 |
| 1.25% | 1.225 |

Figure 40:
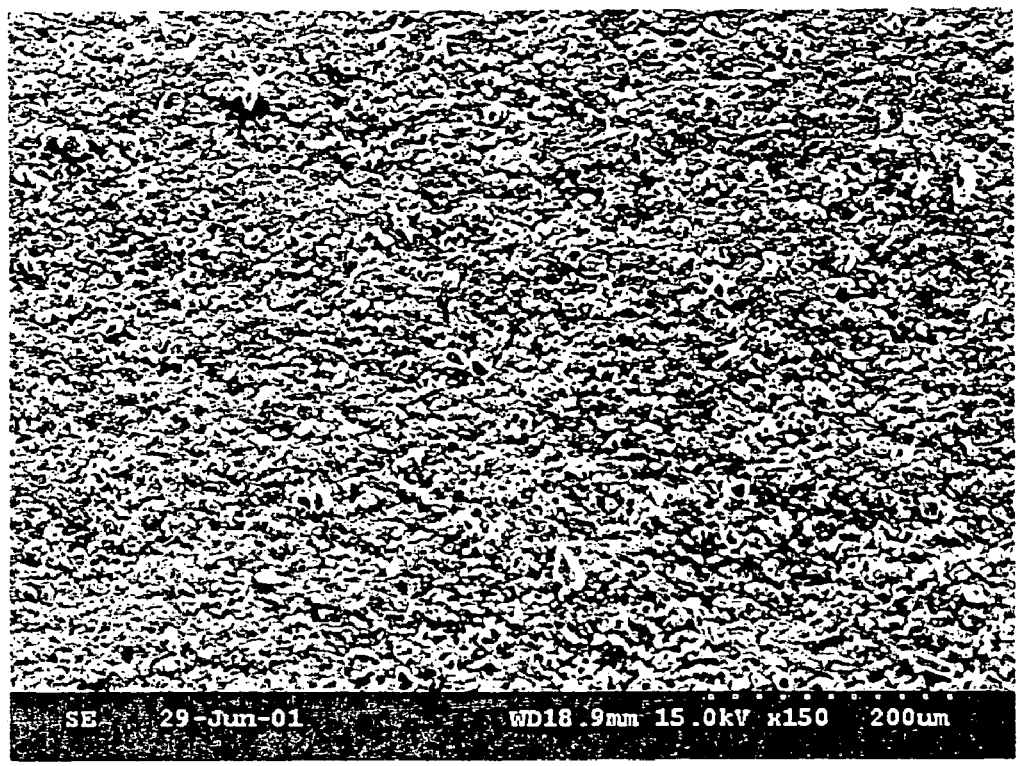
FIG. 40 is a scanning electron photomicrograph according to the present invention with a Powder Free Coagulant glove with a 1.25 weight % microcapsule overdip at a 0% stretch.
Figure 41:
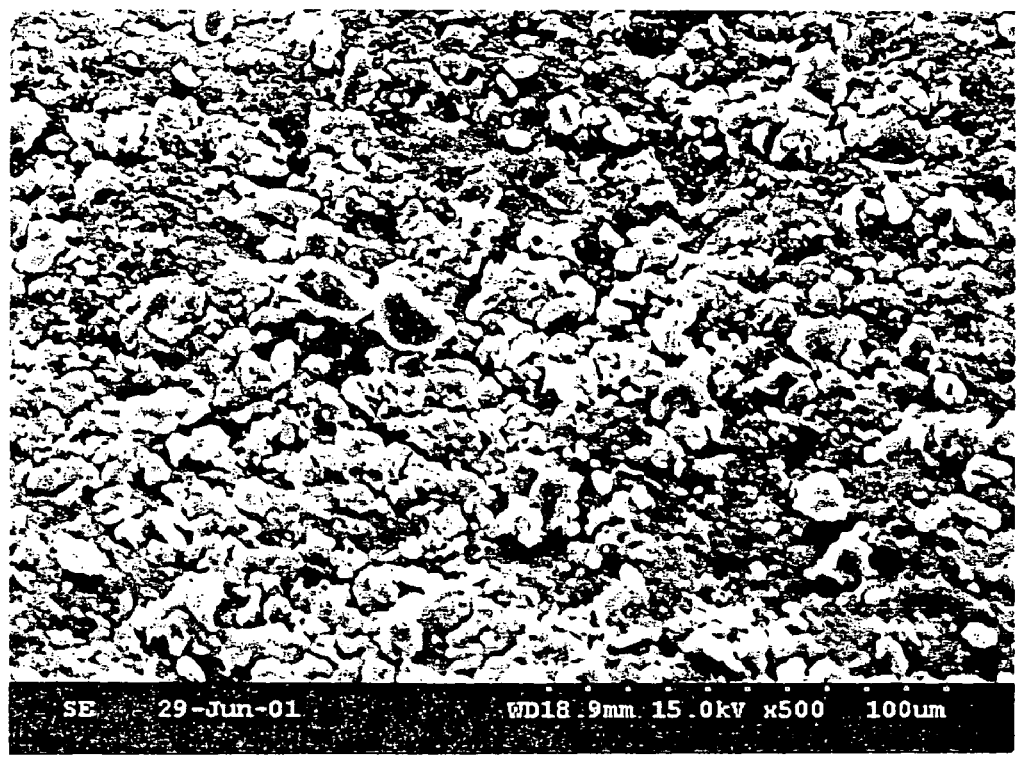
FIG. 41 is a scanning electron photomicrograph according to the present invention with a Powder Free Coagulant glove with a 1.25 weight % microcapsule overdip at a 0% stretch.
Figure 42:
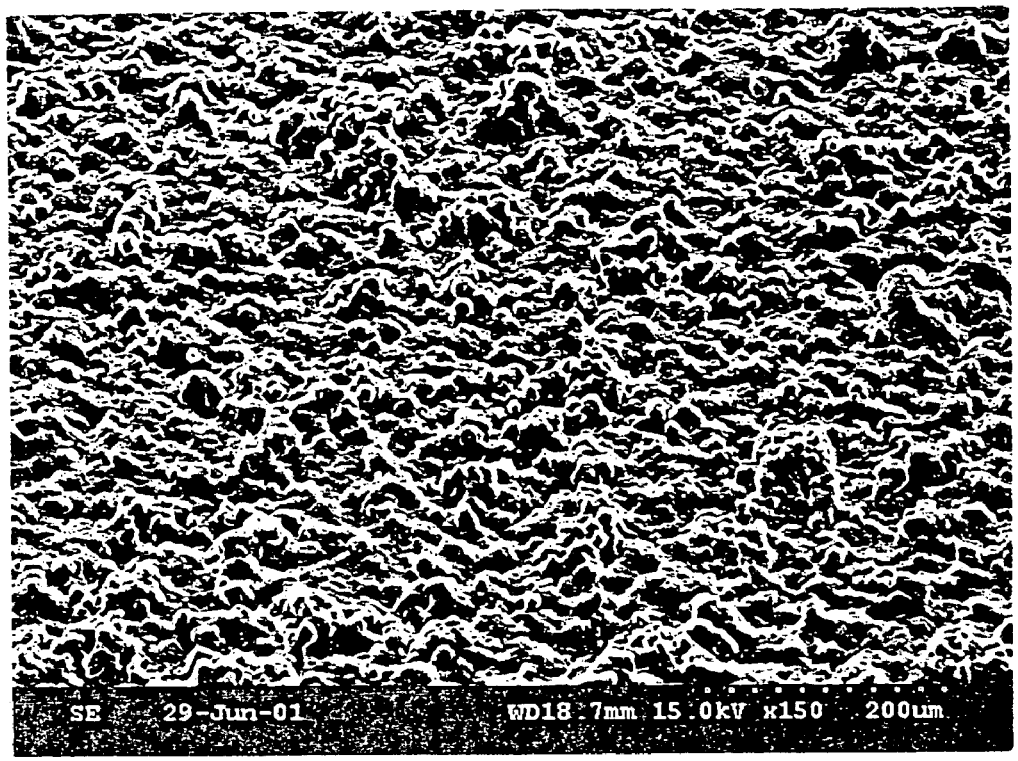
FIG. 42 is a scanning electron photomicrograph according to the present invention with a Powder Free Coagulant glove with a 1.25 weight % microcapsule overdip at a 0% stretch.
Figure 43:
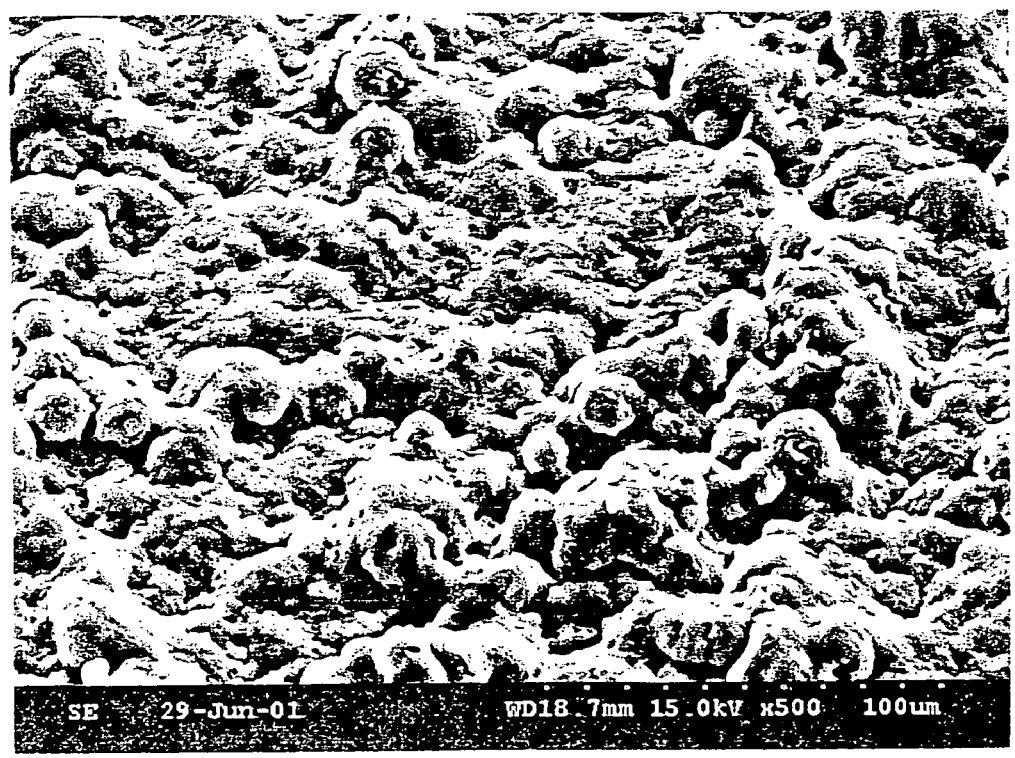
FIG. 43 is a scanning electron photomicrograph according to the present invention with a Powder Free Coagulant glove with a 1.25 weight % microcapsule Overdip at a 0% stretch.

Additionally, the use of the microcapsules in the overdip solution is compatible with the use of a powder free coagulant. FIGS. 40 and 41 illustrate scanning electron photomicrographs of the outside surface of gloves made with a 1.25 weight % microcapsule overdip as illustrated in Table 5 and made by a process including the use of powder free coagulant. FIGS. 42 and 43 show scanning electron photomicrographs of the inside, or donning surface of the gloves made with a 1.25 weight % microcapsule overdip and powder free coagulant. The combined use of a powder free coagulant and a microcapsule overdip in the present invention results in gloves that are easier to don with damp or dry hands and substantially free of particulate matter.

A process for making a glove, using a coating of the present invention, is described as follows. A standard latex coagulant is applied to a clean ceramic former and dried. A standard latex coagulant generally comprises an aqueous solution of a divalent cationic metal salt, a surfactant or wetting agent, and a release powder. The typical divalent metal salt includes, but is not limited to calcium nitrate and the typical class of surfactant or wetting agent is nonionic while the typical release powder is calcium carbonate. Of course, alcohols may be used in lieu of water, other divalent or trivalent cationic metal salts can be used, other surfactant types may be used that are salt stable and other release powders include, but are not limited to starch and talc.

Preferably, the salt is calcium nitrate and the calcium nitrate content is between about 7% and about 50% by weight of the total coagulant content. More preferably, the calcium nitrate content is in a range of about 30% to 45% by weight of the total coagulant content. The coagulating agent most preferably comprises aqueous based calcium nitrate having a solids content of about 60% to about 70% by weight of the raw material. Other divalent cationic metal salts such as, for example, calcium chloride, zinc nitrate, zinc chloride, magnesium acetate, magnesium nitrate, aluminum nitrate and aluminum sulphate may be used individually or in combination with the calcium nitrate.

The ceramic former is dipped into a compounded latex to form a rubber film or laminate layer in the shape of a hand. For example, after the release agent/coagulant dip is applied, a laminate layer is applied to the former. The laminate layer may be comprised of an elastomeric or liquid resin dip, such as natural rubber latex. Alternatively, the laminate layer may be a synthetic rubber, such as synthetic latex, polyurethane, nitrile or polychloroprene. By varying the content of the latex material, the laminate layer may be varied to provide different degrees of strength, comfort and flexibility. In any event, the content of the latex applied to the former will preferably be adjusted to provide the desired gripability, protection from cuts and abrasions and liquid repellency. If desired, the gelled latex film can be overdipped with copolymers of vinyl methyl ether and maleic esters.

After the application of the laminate layer, a second coagulant dip may be applied if another laminate layer is to be applied. The second coagulant dip, which is preferably in the form of a tackifying agent, provides a medium for adherence of the laminate applied in the next step. According to an alternative technique, the formers may be immersed into an adhesive dip to provide strength and a tacky surface for the application of the next laminate layer. Such an adhesive dip may be comprised of any synthetic resin material, and preferably an elastomer. Different degrees of strength and flexibility may be obtained by varying the characteristics of the adhesive material. After application of either a second coagulant dip or an adhesive dip, the next laminate layer is applied.

The gelled latex is then leached in water and dipped in an aluminum sulfate primer. The latex film then enters the coating solution of the present invention having about a 1 weight % to 5 weight % microcapsule overdip. The glove is then passed through ovens at elevated temperatures to dry and cure. Following curing, the glove may be dipped in a silicone emulsion to improve donning and removal from the former.

According to an embodiment of the present invention, there is provided a powder-free coagulant dip. The powder-free coagulant dip comprises a coagulant mixed with water, a surfactant, a detackification agent, an aqueous polychloroprene and an accelerator. Following the curing of the coagulant, an overdip comprising about 1 weight % to about 5 weight % microcapsules, water and polyurethane, the microcapsules including hydrogenated polyisobutene, fragrance, vitamins, moisturizers or dyes and a microcapsule coating having a polyacetal urea may be applied to enhance donnability. In an alternative embodiment, the microcapsule coating may include polyamides and/or gelatin.

According to another embodiment of the present invention, there is provided a further process for making a glove having a coating including microcapsules. A standard latex coagulant, well known to those of ordinary skill in the art, is applied to a clean ceramic former and dried. The gelled latex is leached in water. The leached latex is ordinarily dipped in an aluminum sulfate primer. For this process, however, the latex is not primed with aluminum sulfate but is dipped directly into the donning coating overdip including microcapsules, polyurethane and water. The latex film then enters the coating solution of the present invention. The glove is then passed through ovens at elevated temperatures to dry and cure. Following curing, the glove may be dipped in a silicone emulsion to improve donning and removal from the former.

According to yet another embodiment of the present invention, there is provide a process for making a glove having a coating including microcapsules for improved donning. A standard latex coagulant as described herein is compounded with the coating solution of the present invention having microcapsules, water and polyurethane and is applied to a clean ceramic former and dried. The gelled latex is leached in water. The glove is then cured and treated in the usual manner of post-cure processing as set forth herein.

Another process for making a glove, using a coating of the present invention, may be made by utilizing the present invention as a final dip. A standard latex coagulant, as has been described herein, is applied to a clean ceramic former and dried. The ceramic former is dipped into compounded latex to form a rubber film in the shape of a hand. The gelled latex is leached in water. Additional coatings may be applied over the latex glove, for instance a tackifying agent or an adhesive dip, followed by curing of the glove. The coating in the present invention is prepared as part of a slurry and used as a final dip coating. The glove is then passed through an oven at elevated temperatures to dry and cure the product. Once the glove has been cured, it may be dipped in a silicone emulsion to facilitate improved donning characteristics. In addition, the silicone emulsion improves removal of the glove from the former.

While the invention has been described in conjunction with specific embodiments thereof, it is evident that alternatives, modifications and variations will be apparent to those skilled in the art in light of the foregoing description. Accordingly, it is intended to embrace all such alternatives, modifications and variations as fall within the spirit and broad scope of the appended claims.

What is claimed is:

1. A glove comprising: an outside surface; and an inside skin contacting surface comprising polyurethane-bonded microcapsules, the microcapsules comprising a core material contained within a microcapsule coating, the core material including a low viscosity hydrocarbon, a fragrance, and a vitamin and the microcapsule coating including polyacetal urea or gelatin, wherein a plurality of the microcapsules rupture as a user's hand is being inserted into the glove thereby releasing the core material onto the user's hand.

2. The glove of claim 1 wherein the low viscosity hydrocarbon is selected from the group consisting of hydrogenated polyisobutene, hydrogenated polybutene, and hydrogenated polydecene.

3. The glove of claim 2 wherein the low viscosity hydrocarbon is hydrogenated polyisobutene.

4. The glove of claim 1, wherein the low viscosity hydrocarbon comprises hydrogenated polyisobutene; the fragrance comprises a vanilla fragrance; the vitamin comprises Vitamin A Palmitate and Vitamin E Acetate; and wherein the polyacetal urea comprises a polyoxymethylene urea.

5. The glove of claim 1 wherein the core material comprises moisturizers and dyes.

6. The glove of claim 1, wherein the outside surface comprises a layer formed from an elastomeric material selected from the group consisting of natural rubber latex, polychloroprene, polyurethane, nitrile, or combinations thereof.

7. The glove of claim 1, wherein the core material is lubricious.

8. The glove of claim 1, wherein the core material is moisturizing to the user's hand.

9. The glove of claim 1, wherein the core material facilitates donnability of wet or dry hands.

10. The glove of claim 1, wherein the core material comprises a pleasant odor or fragrance.

11. The glove of claim 1, wherein the microcapsules protrude from the skin contacting surface.

12. A glove comprising: an outside surface; and an inside skin contacting surface comprising polyurethane-bonded microcapsules, the microcapsules comprising a core material contained within a microcapsule coating, the core material including a low viscosity hydrocarbon, a fragrance and a vitamin and the microcapsule coating consisting essentially of polyacetal urea or gelatin, wherein the microcapsules rupture as a user's hand is being inserted into the glove thereby releasing the core material onto the user's hand.

13. The glove of claim 12, wherein the low viscosity hydrocarbon comprises hydrogenated polyisobutene; the fragrance comprises a vanilla fragrance; the vitamin comprises Vitamin A Palmitate and Vitamin E Acetate; and wherein the polyacetal urea comprises a polyoxymethylene urea.

* * * * *